(12) United States Patent
Lauer

(10) Patent No.: US 10,974,038 B2
(45) Date of Patent: Apr. 13, 2021

(54) MEDICAL FUNCTIONAL DEVICE WITH A VALVE SEAT FOR A REMANENT CHECK VALVE

(71) Applicant: FRESENIUS MEDICAL CARE DEUTSCHLAND GMBH, Bad Homburg (DE)

(72) Inventor: Martin Lauer, St. Wendel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 476 days.

(21) Appl. No.: 15/126,260

(22) PCT Filed: Mar. 13, 2015

(86) PCT No.: PCT/EP2015/055298
§ 371 (c)(1),
(2) Date: Sep. 14, 2016

(87) PCT Pub. No.: WO2015/136076
PCT Pub. Date: Sep. 17, 2015

(65) Prior Publication Data
US 2017/0080205 A1    Mar. 23, 2017

(30) Foreign Application Priority Data
Mar. 14, 2014   (DE) ........................ 10 2014 103 507

(51) Int. Cl.
  *A61M 39/24*   (2006.01)
  *A61M 39/26*   (2006.01)
  *A61M 1/36*    (2006.01)

(52) U.S. Cl.
CPC .............. *A61M 39/24* (2013.01); *A61M 1/36* (2013.01); *A61M 39/26* (2013.01);
(Continued)

(58) Field of Classification Search
CPC combination set(s) only.
See application file for complete search history.

(56) References Cited

U.S. PATENT DOCUMENTS 3,941,149 A  *  3/1976  Mittleman ............ A61M 39/24
                                                   137/493.1
D270,881 S       10/1983  Zaro
(Continued)

FOREIGN PATENT DOCUMENTS

CN      1553790      12/2004
CN      1658916       8/2005
(Continued)

OTHER PUBLICATIONS

International Search Report from PCT/EP2015/055298, dated May 19, 2015.
(Continued)

*Primary Examiner* — Guy K Townsend
(74) *Attorney, Agent, or Firm* — Fish & Richardson P.C.

(57) ABSTRACT

A medical functional device with a valve seat for a check valve wherein the check valve is embodied such that it takes, in addition to a first position which is suitable for gas sterilization, a second, functional position, by means of applying force onto a section of the check valve or by means of moving or shifting the section, in which the check valve adopts a check or non-return function, wherein the check valve is embodied such that it remains in the second position after release or shortfall of the force or the moving effect following an accomplished transfer into the second position.

24 Claims, 10 Drawing Sheets

(52) U.S. Cl.
CPC .......... *A61M 2039/242* (2013.01); *A61M 2039/2433* (2013.01); *A61M 2039/2446* (2013.01); *A61M 2039/2453* (2013.01); *A61M 2039/2473* (2013.01); *A61M 2039/2493* (2013.01)

(56) References Cited

U.S. PATENT DOCUMENTS

| | | | |
|---|---|---|---|
| 4,436,620 A | 3/1984 | Bellotti et al. | |
| 4,479,762 A | 10/1984 | Bilstad et al. | |
| 4,666,598 A | 5/1987 | Heath et al. | |
| 4,770,769 A | 9/1988 | Schael | |
| 4,815,705 A * | 3/1989 | Kasugai | B60K 15/0406 137/854 |
| 5,088,515 A * | 2/1992 | Kamen | A61M 39/22 137/15.17 |
| 5,470,483 A | 11/1995 | Bene et al. | |
| 5,628,908 A | 5/1997 | Kamen et al. | |
| 5,653,887 A * | 8/1997 | Wahl | A61M 1/3693 210/745 |
| 5,676,644 A * | 10/1997 | Toavs | A61M 1/3692 604/6.11 |
| 5,702,357 A * | 12/1997 | Bainbridge | A61M 1/30 604/4.01 |
| 5,720,716 A * | 2/1998 | Blakeslee | A61M 1/3652 604/4.01 |
| 5,722,946 A * | 3/1998 | Mudloff | B04B 9/08 604/5.01 |
| 5,738,644 A * | 4/1998 | Holmes | A61M 1/3624 604/4.01 |
| 5,750,025 A * | 5/1998 | Holmes | A61M 1/3639 210/361 |
| 5,783,072 A | 7/1998 | Kenley et al. | |
| 5,795,317 A * | 8/1998 | Brierton | A61M 1/3624 604/6.05 |
| 5,837,150 A * | 11/1998 | Langley | A61M 1/3696 210/782 |
| 5,941,842 A * | 8/1999 | Steele | A61M 1/3624 604/4.01 |
| 6,132,616 A | 10/2000 | Twardowski et al. | |
| 6,165,168 A | 12/2000 | Russo | |
| 6,200,287 B1 * | 3/2001 | Keller | A61M 1/3693 210/767 |
| 6,471,855 B1 | 10/2002 | Odak et al. | |
| 6,481,980 B1 | 11/2002 | Vandlik et al. | |
| 6,537,258 B1 * | 3/2003 | Guala | A61M 39/24 137/522 |
| 6,542,761 B1 | 4/2003 | Jahn et al. | |
| 6,645,166 B2 | 11/2003 | Scheunert et al. | |
| 6,695,803 B1 | 2/2004 | Robinson et al. | |
| 6,709,417 B1 * | 3/2004 | Houle | A61M 5/14224 604/153 |
| 6,752,172 B2 | 6/2004 | Lauer | |
| 6,814,547 B2 * | 11/2004 | Childers | A61M 1/28 210/258 |
| 6,929,751 B2 * | 8/2005 | Bowman, Jr. | A61M 1/28 210/646 |
| 7,488,301 B2 | 2/2009 | Beden et al. | |
| 7,648,627 B2 | 1/2010 | Beden et al. | |
| 7,686,779 B1 * | 3/2010 | Gibbs | A61M 1/30 604/6.01 |
| 7,789,849 B2 * | 9/2010 | Busby | A61M 1/28 604/29 |
| 7,887,520 B2 * | 2/2011 | Simon | A61M 5/16804 604/248 |
| 7,935,074 B2 | 5/2011 | Plahey et al. | |
| 8,142,653 B2 | 3/2012 | Beden et al. | |
| 8,192,401 B2 * | 6/2012 | Morris | A61M 1/14 604/153 |
| 9,180,240 B2 * | 11/2015 | Farrell | F04B 43/026 |
| 9,421,314 B2 * | 8/2016 | Plahey | A61M 1/16 |
| 9,500,188 B2 * | 11/2016 | Ly | F04B 17/042 |
| 10,117,985 B2 * | 11/2018 | Ly | G01F 22/00 |
| 2002/0032398 A1 * | 3/2002 | Steele | A61M 1/3696 604/6.01 |
| 2002/0033370 A1 * | 3/2002 | Bainbridge | A61M 1/30 210/782 |
| 2002/0041825 A1 | 4/2002 | Scheunert et al. | |
| 2002/0062109 A1 * | 5/2002 | Lauer | A61M 1/367 604/256 |
| 2003/0042181 A1 | 3/2003 | Metzner | |
| 2003/0130607 A1 | 7/2003 | Delnevo et al. | |
| 2004/0019313 A1 * | 1/2004 | Childers | A61M 1/28 604/5.01 |
| 2004/0079707 A1 | 4/2004 | Smith et al. | |
| 2004/0084647 A1 | 5/2004 | Beden et al. | |
| 2004/0186416 A1 | 9/2004 | Caleffi | |
| 2004/0267228 A1 * | 12/2004 | Hattori | A61J 1/1406 604/406 |
| 2005/0017505 A1 * | 1/2005 | Thilly | A61M 39/18 285/45 |
| 2005/0045548 A1 | 3/2005 | Brugger et al. | |
| 2005/0131332 A1 * | 6/2005 | Kelly | A61M 1/1633 604/4.01 |
| 2005/0230292 A1 | 10/2005 | Beden et al. | |
| 2005/0283132 A1 | 12/2005 | Stanus et al. | |
| 2006/0079826 A1 | 4/2006 | Beden et al. | |
| 2006/0155236 A1 | 7/2006 | Gara et al. | |
| 2006/0224099 A1 | 10/2006 | Hutchinson et al. | |
| 2006/0226087 A1 * | 10/2006 | Robinson | A61M 1/3693 210/787 |
| 2006/0226090 A1 * | 10/2006 | Robinson | A61M 1/3693 210/787 |
| 2006/0237351 A1 | 10/2006 | Felding | |
| 2006/0254982 A1 | 11/2006 | Kopperschmidt | |
| 2006/0289360 A1 | 12/2006 | Delnevo et al. | |
| 2007/0112297 A1 | 5/2007 | Plahey et al. | |
| 2007/0232980 A1 * | 10/2007 | Felt | A61M 1/0209 604/6.1 |
| 2007/0243990 A1 | 10/2007 | Kolenbrander et al. | |
| 2007/0253463 A1 * | 11/2007 | Perry | G01K 1/08 374/208 |
| 2007/0278155 A1 * | 12/2007 | Lo | A61M 1/166 210/646 |
| 2007/0286756 A1 | 12/2007 | Jones et al. | |
| 2008/0058712 A1 | 3/2008 | Plahey | |
| 2008/0058727 A1 * | 3/2008 | Domash | A61M 39/10 604/174 |
| 2008/0097283 A1 | 4/2008 | Plahey | |
| 2008/0105600 A1 | 5/2008 | Connell et al. | |
| 2008/0105601 A1 | 5/2008 | Ikeda | |
| 2008/0169444 A1 | 7/2008 | Guala | |
| 2008/0185062 A1 | 8/2008 | Johannes Nijland | |
| 2008/0202591 A1 * | 8/2008 | Grant | F04B 49/22 137/12 |
| 2008/0208159 A1 | 8/2008 | Stanus et al. | |
| 2008/0228125 A1 | 9/2008 | Brugger et al. | |
| 2009/0008331 A1 * | 1/2009 | Wilt | A61M 1/1621 210/647 |
| 2009/0095679 A1 * | 4/2009 | Demers | G16H 40/63 210/646 |
| 2009/0099498 A1 * | 4/2009 | Demers | A61M 1/106 604/6.09 |
| 2009/0105657 A1 | 4/2009 | Domash et al. | |
| 2009/0124963 A1 * | 5/2009 | Hogard | A61M 1/14 604/30 |
| 2009/0198170 A1 * | 8/2009 | Childers | A61M 1/16 604/6.09 |
| 2010/0100034 A1 | 4/2010 | Wich-Heiter | |
| 2010/0133153 A1 * | 6/2010 | Beden | A61M 1/3496 210/85 |
| 2010/0192686 A1 * | 8/2010 | Kamen | A61M 1/365 73/290 R |
| 2010/0200486 A1 * | 8/2010 | Gunther | A61M 1/16 210/188 |
| 2010/0274169 A1 * | 10/2010 | Lauer | A61M 39/22 604/6.1 |
| 2012/0080437 A1 * | 4/2012 | Guenther | A61M 1/14 220/501 |

(56) References Cited

U.S. PATENT DOCUMENTS

| | | | | |
|---|---|---|---|---|
| 2013/0020237 | A1* | 1/2013 | Wilt | A61M 1/341 210/85 |
| 2013/0131581 | A1* | 5/2013 | Lundtveit | A61M 1/1664 604/28 |
| 2014/0199193 | A1* | 7/2014 | Wilt | F04B 43/0054 417/477.2 |
| 2014/0299544 | A1* | 10/2014 | Wilt | A61M 1/1601 210/646 |
| 2017/0014566 | A1 | 1/2017 | Childers et al. | |
| 2017/0080141 | A1* | 3/2017 | Lauer | A61M 1/267 |
| 2017/0080204 | A1* | 3/2017 | Lauer | A61M 39/20 |
| 2017/0080205 | A1* | 3/2017 | Lauer | A61M 39/26 |
| 2017/0136169 | A1* | 5/2017 | Lauer | A61M 1/14 |
| 2017/0189596 | A1* | 7/2017 | Lauer | A61M 1/16 |

FOREIGN PATENT DOCUMENTS

| | | |
|---|---|---|
| CN | 101224320 | 7/2008 |
| CN | 101466421 | 6/2009 |
| CN | 102458505 | 5/2012 |
| DE | 19837667 | 3/2000 |
| DE | 10053441 | 5/2002 |
| DE | 10224750 | 12/2003 |
| DE | 102004011461 | 9/2005 |
| DE | 102007018362 | 10/2008 |
| DE | 102007042964 | 3/2009 |
| DE | 102009008346 | 8/2010 |
| DE | 102009012632 | 9/2010 |
| DE | 102009012633 | 9/2010 |
| DE | 102009018664 | 10/2010 |
| DE | 10 2009 024469 A1 | 1/2011 |
| DE | 102009024469 | 1/2011 |
| DE | 102009036101 | 2/2011 |
| DE | 10 2010 032181 A1 | 1/2012 |
| DE | 102010032181 | 1/2012 |
| EP | 0611227 | 8/1994 |
| EP | 0952858 | 11/1999 |
| EP | 0980686 | 2/2000 |
| EP | 1661599 | 5/2006 |
| EP | 1946793 | 7/2008 |
| EP | 1953432 | 8/2008 |
| FR | 2594340 | 8/1987 |
| GB | 2110564 | 6/1983 |
| JP | 51-070530 | 6/1976 |
| JP | 62-005355 | 1/1987 |
| JP | S63-135670 | 6/1988 |
| JP | 05-507015 | 10/1993 |
| JP | 2001-504374 | 4/2001 |
| JP | 2001-129080 | 5/2001 |
| JP | 2001-252362 | 9/2001 |
| JP | 2002-177383 | 6/2002 |
| JP | 2003-518964 | 6/2003 |
| JP | 2003-533243 | 11/2003 |
| JP | 2004-521707 | 7/2004 |
| JP | 2005-508719 | 4/2005 |
| JP | 2005-528168 | 9/2005 |
| JP | 2006-500076 | 1/2006 |
| JP | 2006-026270 | 2/2006 |
| JP | 2007-117210 | 5/2007 |
| JP | 2008/500070 | 1/2008 |
| JP | 2008-531192 | 8/2008 |
| JP | 2008-272440 | 11/2008 |
| JP | 2010-188164 | 9/2010 |
| JP | 2012-524558 | 10/2012 |
| KR | 2008-0009208 | 1/2008 |
| TW | 200824731 | 6/2008 |
| WO | WO 95/17603 | 6/1995 |
| WO | WO 03/101510 | 12/2003 |
| WO | WO 2005/044339 | 5/2005 |
| WO | WO 2005/087290 | 9/2005 |
| WO | WO 2005/116497 | 12/2005 |
| WO | WO 2006/122400 | 11/2006 |
| WO | WO 2007/146586 | 12/2007 |
| WO | WO 2008/011220 | 1/2008 |
| WO | WO 2008/053262 | 5/2008 |
| WO | WO 2008/099890 | 8/2008 |
| WO | WO 2009/033511 | 3/2009 |
| WO | 2010-102784 A1 | 9/2010 |
| WO | WO 2010/102784 | 9/2010 |
| WO | WO 2010/102790 | 9/2010 |
| WO | WO 2011/015309 | 2/2011 |

OTHER PUBLICATIONS

International Search Report and Written Opinion in Application No. PCT/EP2015/055298, dated May 19, 2015, 12 pages.
International Preliminary Report on Patentability in Application No. PCT/EP2015/055298, dated Sep. 14, 2016, 10 pages.
minivalve.com [online] Retrieved from the Internet Mar. 13, 2020, URL: <http://minivalve.com/newsite/index.php/de/by-type/umbrella-valves/components>, 1 page.

* cited by examiner

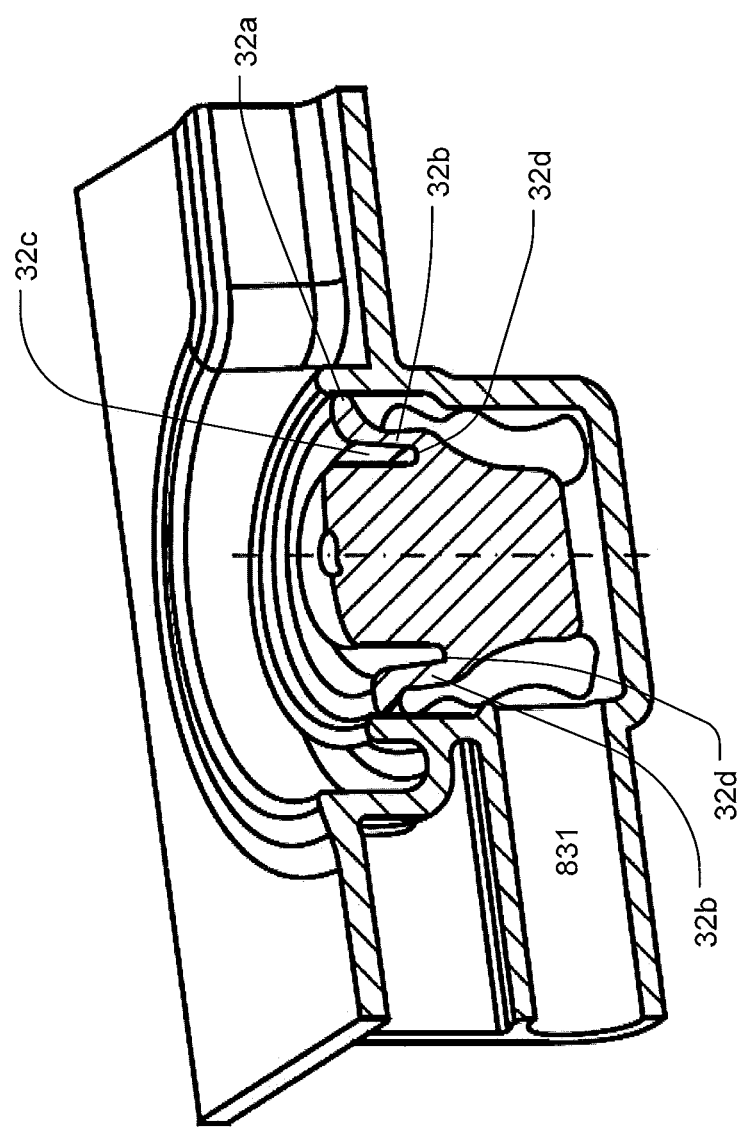

MEDICAL FUNCTIONAL DEVICE WITH A VALVE SEAT FOR A REMANENT CHECK VALVE

CROSS REFERENCE TO RELATED APPLICATIONS

The present application is the national stage entry of International Patent Application No. PCT/EP2015/055298, filed on Mar. 13, 2015, and claims priority to Applications No. DE 10 2014 103 507.0, filed in the Federal Republic of Germany on Mar. 14, 2014, the disclosures of which are expressly incorporated herein in its entirety by reference thereto.

FIELD OF THE INVENTION

This disclosure relates to a medical functional device.

BACKGROUND

Single-use systems are being increasingly realized in the medical or laboratory technology as compact medical functional devices such as cassette systems or blood treatment cassettes in which liquids and gases, in particular medical fluids and blood, are conducted in channels and chambers.

The functional element of the check valve is used in those cassette systems, however also as a single assembly inserted into tubes, to lock the flow of fluids passively, i.e. without the presence of actively driven or powered valves, in the desired counter-flow direction and to release it in the desired direction of flow, often only starting from a certain opening pressure.

Some cassette disposables (also denoted as single-use cassettes) of the applicant of the present invention consist substantially of a hard part made or produced by means of injection or coating technique and have fluid conducting structures as well as a film. The film closes or locks, after its pressing to, gluing to or welding on the hard part, hard-part channels and chambers, which are half-side open, such that they are fluid-tight. In addition to its closing or locking function, the film also allows, due to its flexibility and thin wall-thickness, the measuring of parameters such as temperatures, pressures and fill levels, the detection of air and blood as well as the actuation of valves and the activation of check valves through the film. Such check valves may, in such cassettes, serve to prevent the backward flow of contaminated dialyzer fluid into the hydraulic or water section of the treatment machine (in short: machine), to prevent the escape of blood across the arterial heparin luer connection and the venous addition luer connection in case of malfunction of the machine or faulty operation by the user, to avoid the penetration of air in the cassette below a given opening pressure (underpressure or vacuum to the environment) and to prevent the outflow of contaminated residual fluid in the environment during the removal of the disposable.

Most of the disposable systems must be sterilized, wherein depending on the material of the disposable, gas treatments such as ETO, steam vacuum and the $H_2O_2$ sterilization are also used besides the radiotherapies gamma and ebeam. When performing the gas sterilization a problem may arise in that surfaces extensively contacting or touching each other and obstructed or throttled fluid paths may hamper or complicate or render impossible the sterilization. Therefore, some check valves possess a first, primarily flow-open "initial" position for ensuring the gas sterilizibility. The check valve is transferred out of the initial position into a second, so-called "activated" position when the blood treatment apparatus is being equipped with the cassette. Only at the point of this transfer, denoted here as activation, the valve has the function of non-return; not already beforehand. Such an activatable check valve emerges for example from the patent application DE 10 2009 024 469.7, as filed with the German Patent and Trademark office on Jun. 10, 2009 for the applicant of the present application.

The activatable check valve, mentioned supra, is activated when the machine door is closed after equipping the blood cassette in the dialysis machine. The activation takes place when the check valve is moved or shifted, by means of a hump protruding out of an actuator-sensor-unit, under denting the film of the disposable, as far in the valve seat of the cassette such that the ring-shaped sealing seat area of the elastomer component and the hard component come to be positioned, with prestressing or bias, on top of each other. Through this, the fluid-open initial position (denoted herein also as first position) will be left and the check valve position (denoted herein also as second position) is engaged or taken. The clamping alignment ribs of the elastomer components comprise only a little oversize or excess with regard to the associated clamping alignment bore in the hard part. In this way, the safe gas sterilization is initially ensured. Subsequently, the reliable non-return function or check function is activated.

SUMMARY

This document describes medical functional devices having at least one check valve (herein also denoted as check valve arrangement).

The object of the present invention may be solved by a medical functional device having features described herein.

Embodiments of a medical functional device having a valve seat for a check valve, also denoted as check valve arrangement or, in short as valve, are described herein.

The check valve can be embodied such that it takes, in addition to a first position, suitable for the gas sterilization, by which a sterilization split or slot remains or is maintained, a second functional position. This takes place by means of applying force on a section of the check valve and/or a movement or shift of the section. The first functional position is herein also called initial position or sterilizing position. The second functional position is herein also called activated position or non-return position.

In the second, functional position, the check valve adopts a non-return function, wherein the check valve is embodied such that it remains in the second position after release of force following completed transfer into the second position.

After release of the transferring force or after disengaging the moving or shifting actuator out of or from the check valve, the check valve does not indicate any, or in any case, any sufficient non-return effect by means of which the check valve would be brought by itself from the non-return position back into the sterilization position. The check valve can be denoted as self-retaining or latching.

The transition from the first position into the second position is also denoted herein as "activation".

A check valve which independently remains in the second position following a release of the force which has effected or caused the transition from the first position into the second position, is herein also denoted as "remanently activated". A valve suitable thereto is, hence, also regarded and/or denoted as "remanently activatable".

In all of the following embodiments, the use of the expressions "may be" or "may have" etc., is to be understood synonymously with "preferably is" or "preferably has" etc., respectively, and is intended to illustrate an exemplary embodiment according to the present invention.

Whenever a numerical word is mentioned herein, the skilled person understands this as an indication of a numerical lower limit. Provided it does not lead to any contradiction discernible for the skilled person, the skilled person in these cases implicitly understands for example "one" always as "at least one". This understanding is also encompassed by the present invention as well as the interpretation that a numeric word, for example, "one" can alternatively be meant as "exactly one", wherever this is technically possible in the view of the skilled person. Both are encompassed by the present invention and apply to all used numerical words herein.

Advantageous developments of the present invention are the subject-matter of dependent claims and embodiments respectively.

Embodiments according to the present invention may comprise one or more of the following features in any arbitrary combination.

In some of the exemplary embodiments according to the present invention, the cap may be embodied as a snap-in cap.

In some exemplary embodiments of the functional device according to the present invention, the actuating of the valve generally takes place through an impression of a path/a movement. The force mentioned herein is then a reaction thereupon.

In some particular exemplary embodiments of the functional device according to the present invention, the check valve has no non-return function in the first position.

In some exemplary embodiments of the medical functional device according to the invention, the check valve is embodied such that it is transferred by means of an actuator of a blood treatment apparatus from the first position into the second position. Thereby, the functional device is connected for its operation with the blood treatment apparatus.

In some particular exemplary embodiments according to the present invention, the functional device is embodied such that the check valve remains in the second position, through friction closure, following release of the force. For that purpose, an element may be provided which grants a friction closure, e.g., between at least one section of a valve body and at least one section of a valve seat. This element may also be denoted as friction-closure element.

In some exemplary embodiments of the functional device according to the present invention, the check valve comprises or is a valve body and/or a cap which whenever mentioned herein, may optionally be embodied as snap-in cap; in these embodiments, the valve seat is not part of the check valve. Whereas, in other exemplary embodiments according to the present invention the valve seat is also part of the check valve.

In certain exemplary embodiments according to the present invention, the functional device is embodied such that the check valve, following release of the force, remains in the second position only through friction closure.

In specific exemplary embodiments according to the present invention, the functional device is embodied such that the check valve (or the valve body and/or the cap) is shifted relative to the valve seat or to the rest of the functional device during or for the transfer of the check valve from the first position into the second position. The movement relative to the valve seat may thereby take place in a direction which is preferably completely or substantially vertical to the film plane.

In certain exemplary embodiments according to the present invention, the functional device is embodied such that the cap, where available, does not move relative to the valve seat when the check valve is being opened.

In some exemplary embodiments of the functional device according to the present invention, the check valve comprises a valve body and a separately thereof produced or manufactured cap or snap-in cap.

In some particular exemplary embodiments of the functional device according to the present invention, the valve body comprises a number of knobs. They radially extend out of the openings or through-openings of the cap, after the connection of the valve body with the cap.

In certain exemplary embodiments of the functional device according to the present invention, both the valve body and the cap comprise drainage structures.

In some exemplary embodiments of the functional device according to the present invention, a step or layer or a step-like diameter restriction is embodied within the cylinder-shaped section of the valve seat of the cassette in the support ring area.

In some particular exemplary embodiments of the functional device according to the present invention, the valve seat and/or the sealing section present in the sealing area are designed conically or flat. The valve body and/or the cap seal against the sealing area.

In certain exemplary embodiments of the functional device according to the present invention, the valve body is radially positioned in the cap under a first prestressing or bias and axially under a second prestressing or bias. Hereby, the second prestressing or bias may be larger the first one.

In some exemplary embodiments of the functional device according to the present invention, the valve body has the form of a cup with a valve tray and optionally has a centrally, and exemplary, stiffly-fastened tension rod at the valve tray. Thereby, the tension rod is designed for connecting the valve body with the cap while the rod tension is snapped-in or engaged in a snap-in opening of the cap.

In some particular exemplary embodiments of the functional device according to the present invention, the cap comprises tongues or pins which extend radially.

In certain exemplary embodiments of the functional device according to the present invention, the rod tension and a valve tray are sufficiently stiff such that the rod tension in the cap maintains in the second position, in all spatial directions, a contact-free space to further sections.

In some exemplary embodiments of the functional device according to the present invention, the rod tension and the valve tray are sufficiently stiff such that the rod tension in the cap maintains in the second position, in all spatial directions, a contact-free space to all sections.

In some particular exemplary embodiments of the functional device according to the present invention, the cap has the form of an arch having several openings or through-openings which are open radially to the outside or outwardly and axially at the top. Further, snap-in tongues or pins are arranged in the through-openings, which only partially cover the openings or through openings when they are radially inwardly bent.

In certain exemplary embodiments of the functional device according to the present invention, the number of through-openings and the snap-in tongues or pins is uneven, respectively.

In some particular exemplary embodiments of the functional device, the check valve is embodied such that it remains due to locking in place, jamming, wedging or the like of components of the check valve with each other in the second position, on the one hand side after the second position has been reached and on the other hand side after shortfall of the force or after release of the moving actuator from the check valve. These components may be the valve body and the cap, wherein the valve body may, through the application of force or by means of the moving actuator, be elastically deformed snapped in or locked in place, jammed, wedged or the like in the cap. In certain embodiments according to the present invention, it is thereby a support ring of the valve body which snaps in, jams or wedges behind or beneath sections of the cap, such as the optional support tongues or pins of the cap, while a further section of the valve body, such as an optional centering cone, presses therefrom under effect of a spring element against an again further section of the cap, such as an optional cone reception.

The spring element in certain exemplary embodiments of the functional device according to the present invention is designed as an elastical section, preferably of the valve body. The spring element may be a spring membrane. The spring membrane may be closed or peripheral and/or rotationally symmetric. The spring membrane may have, in a cut, a cup-shaped section. The spring membrane may comprise in a cut concentric sections.

In some particular exemplary embodiments of the functional device according to present invention, the check valve or a section thereof, is embodied to effect or causes a prestress of the check valve, which is inserted in the valve seat, or of at least one section thereof.

In some exemplary embodiments of the functional device according to the present invention, the prestress is effected by means of a spring element which is exemplary a spring membrane.

In some particular exemplary embodiments of functional device according to the present invention, the spring element is a section of the valve body.

In some exemplary embodiments of the functional device according to the present invention, the cap comprises a closed or peripheral edge. This is located at the level of the snap-in tongue or pin and forms thereby the main separation plane of the injection molding. The complete or peripheral edge may in certain exemplary embodiments of the present invention effect or causes a deviation of the cap from the cylinder form which may advantageously prevent a canting or jamming of the cap when it is tilted or subject to tilting movements.

In some particular exemplary embodiments of the functional device according to the present invention, a closed or peripheral slot or split, denoted herein as sterilization slot, remains in the first position. This axial mounting position and therewith the sterilization slot or split are held up in the form of clamping centering ribs as an example of a friction closure element, through friction closure of components contacting each other, preferably valve seat on the one end and valve body on the other end. The sterilization slot may be flowed through by sterilization fluid in the first position. It is closed in the second position or does not exist anymore.

In certain exemplary embodiments according to the present invention, the functional device is designed as blood cassette, cassette, blood tube or infusion tube.

In some exemplary embodiments according to the present invention, the functional device is designed as a blood cassette which comprises a hard body and a film covering the hard body or parts thereof. Thereby, the valve seat is provided in the hard body. The check valve is arranged such that it is transferred into the second position by means of pressure or moving or shifting of an actuator of the blood treatment apparatus on the film.

In some particular exemplary embodiments of the functional device according to the present invention, the film-sided front end surface of the check valve does not extend or project beyond the film plane of the blood cassette.

In certain embodiments according to the present invention, a one-piece valve body is made up of silicon rubber. The valve body may comprise a preferably cup-shaped radial sealing bar, which is fastened to the corn cylinder in a closed or peripheral fluid-tight manner.

In certain embodiments according to the present invention, the valve body comprises guiding clamping drainage ribs, which serve for guiding, clamping and draining. They are preferably fastened to the corn cylinder in an equal and odd-numbered pitching and in a preferred number of more the 2.

The valve seat may in certain embodiments according to the present invention comprise two adjacent cylinders, here, being a guiding cylinder (down in the valve seat) and a sealing cylinder (at the top in the valve seat), wherein the sealing cylinder has a larger diameter than the guiding cylinder, and wherein the area of the diameter transition or stage or step between both cylinders is denoted as snap-in transition or step. At least some of the clamping guiding knobs of the valve body or the guiding clamping drainage ribs are positioned in the first position at the guiding cylinder. The clamping snap-in knobs which extend or project beyond the aforementioned clamping guiding knobs are positioned in the first position at the sealing cylinder. Both clamping snap-in knobs and aforementioned clamping guiding knobs are positioned at the guiding cylinder in the second position.

In certain embodiments according to the present invention, a radial sealing bar of the valve body is not axially meshed to the sealing cylinder, therefore there is a fluid-open ring volume (a sterilization slot). Only by operational discharge of an axial minimum activation force (preferred is 20 to 40 N) onto the front end surface of the core cylinder, a shifting movement is introduced.

Drainage bottom ribs are located in certain embodiments according to the present invention, in the second position, at a lower section, e.g. the bottom, of the guiding cylinder. They may hereby limit the activation hub and ensure, together with all the other ribs, the equal de-aeration and circulation properties of the valve body as well as the safe strelizability by means of gases.

In certain embodiments according to the present invention, the closed or peripheral radial sealing bar, preferably having a pointed sealing edge, forms a check valve sealing system together with the sealing cylinder of the valve seat of the cassette, and that after an activation hub has been executed. Thereby, the closed sealing edge of the valve body—preferably made from elastomer—abuts on the sealing cylinder under radial prestressing or bias.

In certain embodiments according to the present invention, the valve body consists of an elastomer material, preferably of silicon rubber.

In certain embodiments of the present invention, the positioning ring of the valve body comprises several drainage structures, preferably peripherally arranged, which ensure in the mounted state the accessibility for the sterilizing gases.

In certain embodiments according to the present invention, the upper ring front end surface of the positioning ring sits flush or level with the film or the cassette edge on or at which the film is hung up or welded.

In certain embodiments according to the present invention, an outer envelope surface of the positioning ring comprises a larger diameter than the landing or change bore attached thereto in the cassette. Through the diameter difference, the hardness of the material and/or the design of the drainage structures a retention force caused by friction may arise.

In certain embodiments according to the present invention, a lower ring front end surface of the positioning ring serves as movement stop and therewith "activating" the calibration of the opening pressure and the outlet characteristic line in the second position.

In certain embodiments according to the present invention, an outlet ring zone consists of single, spiral, loop-shaped single bars having slots in between. It serves for the fluid outlet into the second position, holds the valve core in the set position and builds an axially springy and tilting-position compensating support structures.

In certain embodiments according to the present invention, the valve body comprises a preferably mushroom-shaped valve core. The latter comprises a preferably stiffer core area which acts as movement limitation in both axial movement directions, i.e. at its upper side against the film and at its lower side against a cassette-sided plunger.

The stoppers are touched only when the specified pressure and volume flow area is left. A sealing ring zone of the valve comprises in the first position a ring slot—of e.g. ca. 0.4 mm—for the safe gas sterilization. In the second position, it seals, preferably under minimum prestressing or bias of ca. 0.4 mm, against, for example a conical or flat, sealing seat of the valve seat.

In certain embodiments according to the present invention, the check valve arrangement comprises or consists of a valve body having a cap. The cap is preferably made from thermoplastic, preferably, polypropylene (in short: PP).

In certain embodiments according to the present invention, the valve body having a sealing ring comprises a number of knobs which radially outwardly project out of openings of the cap after the pre-assembly of the valve body with the cap.

In certain embodiments according to the present invention, both the valve body and the cap comprise drainage structures. They serve for the optimal gas and vapor sterilizability.

In certain embodiments according to the present invention, a step (step-like diameter restriction) denoted as diameter landing or change is provided within the cylinder-shaped section of the valve seat of the cassette in the support ring space. An activation or the second position is reached when the knobs, radially protruding beyond the diameter landing, are shifted into the valve seat of the cassette and/or when a ring front end area of the cap has come closer, up to an extended contact, to a ring front end area of the valve seat.

In certain embodiments according to the present invention, the cap is stiffer in comparison with the valve body.

In certain embodiments according to the present invention, the check valve arrangement according to the present invention may be two-piece.

In certain embodiments according to the present invention, the check valve arrangement may seal in a flat manner. "Flat" means in specific embodiments according to the present invention that the sealing area is, preferably completely, substantially or partially plane and/or parallel to a film plane. The sealing area, in some particular embodiments according to the present invention, may preferably completely or substantially be positioned in a plane which is perpendicular to the shifting direction of the valve body.

In certain embodiments according to the present invention, the valve seat against which the valve body and/or the cap seals in the second position, is embodied, in the sealing area, conically or in cross-section cone-shaped.

In certain embodiments according to the present invention, the valve body has the shape of a cup with a bellows-type envelope, an optional largely flat, stiffly-designed valve body and an optional tension rod, which is centrally and stiffly attached to the valve tray. The tension rod is designed for the connection between valve body and cap, e.g., as the rod tension is snapped in a suitable central snap-in opening of the cap.

The ring front end of the bellows envelope facing away from the valve body is positioned in certain embodiments according to the present invention radially, under, preferably, lighter prestressing or bias and axially under larger prestressing or bias than radially in the cap. Thereby, the bellows envelope is correspondingly compressed and the axial prestressing or bias on the snapped in rod tension is maintained. This axial prestressing or bias may be denoted herein as prestressing or bias of the check valve.

The cap, in certain embodiments according to the present invention, is made from the relatively stiff material PP (bending modulus of elasticity ca. 1750 N/mm)

The cap, in certain embodiments according to the present invention, is designed with radially springy tongues or pins.

In certain embodiments according to the present invention, the rod tension and the valve tray are embodied sufficiently stiff so that the rod tension maintains in the second position a contact-free space to the mounting surrounding in all spatial directions.

In certain embodiments according to the present invention, the cap or cap (both expressions are to be understood as interchangeable provided the cap can be snapped in the respective embodiments) additionally comprises at a lower ring front end several locking lugs which are radially inwardly abutting or protruding.

The cap, in certain embodiments of the present invention, is designed so that it may be produced in a multiple on-off injection molding with central hot channel gatings, respectively.

The valve body comprises, in certain embodiments according to the present invention, a central conical pin, which is received in a play-free manner in a corresponding cone of the cap.

A connecting membrane or membrane extends, in certain embodiments according to the present invention, between cone and a support sealing ring of the valve body.

In certain embodiments according to the present invention, the valve body comprises, in an un-built-in state, a slight warping, facing the bottom, of its connecting membrane which is centrally arranged, i.e. in a fully assembled state towards the valve seat of the medical functional device.

In the pre-assembly of the valve body into the cap, this curvature is, in certain embodiments according to the present invention, already neutralized through a snap-in of a support flange of the valve body until its toothing with the retaining lugs of the cap, or the connecting membrane is already so elastically deformed that a light curvature takes place in the opposite direction, hence upwardly, i.e. away from the valve seat. The curvature in opposite direction strengthens once again, in certain embodiments according to the present invention, during or through activation or transition into the second position. In certain embodiments according to the present invention, the curvature is strengthened once again during or through its flow-through with treatment fluid.

In certain embodiments according to the present invention, the support sealing ring is more compact and/or thick-walled in relation to the connecting membrane.

The check valve arrangement in certain embodiments according to the present invention has the form of a pin plate in cap.

In certain embodiments according to the present invention, the valve seat does not comprise any undercuts.

In certain embodiments according to the present invention, the cap has the form of an arch with several through openings which are radially to the outside or axially to the top open. Snap-in tongues or pins which may be bent radially outwardly are arranged in these through openings snap-in tongues or pins close the through openings only proportionally, e.g. to ca. 30%.

Spatial indications like "top", "bottom" and so on, refer in case of doubt to the illustrations as can be seen in the attached figures.

In certain embodiments according to the present invention, the number of the through openings and the number of the snap-in tongues or pins are preferably uneven, respectively.

In certain embodiments according to the present invention, the cap comprises a peripheral, preferably, sharp edge which is preferably positioned in both the supporting arches and the bendable snap-in tongues or pins at the same level and thereby forming the main separation plane of the injection molding.

In certain embodiments according to present invention, an upper ring front end of a cap forms the highest section of the arch construction and represents through the film the mechanical cutting point for the leading-in of activation force, activation path and retention force by the actuator-sensor-unit of the treatment machine. It represents a flat ring front end that is interrupted by structuring notches or chamfers.

In certain embodiments according to the present invention, the cap comprises at both the upper ring front end and in the area of the cone reception numerous patterns or structurings like structuring notches or chamfers, grooves and recesses.

In order for a part to maintain a symmetrical—and by the cooling of the thermoplastic during the production—warping or deformation-unremarkable form, the outer and inner patterns are, in certain embodiments according to the present invention, arranged concentrically with the same number or with an even number divided in relation to the number of the through openings or snap-in tongue or pins.

In certain embodiments according to the present invention, the cap comprises not only the arch structure, rather also the vertical cylinder walls and conical, in particular, steep conical peripheral, walls, preferably inside and outside of a cap aligning notch.

The valve body has or is, in certain embodiments according to the present invention, a form similar to rolling bellow and encompasses an aligning cone, stop front end, at least two support aligning humps, a spring connecting membrane, a sealing ring and a support ring, wherein the foregoing expressions are described below, with reference to FIG. 6.

In certain embodiments according to the present invention and in order to additionally increase the insertion possibility, both the lower ring front end of the cap and the valve seat edge are provided with curves which act as additional insertion chamfers.

In certain embodiments according to the present invention, the snap-in tongues or pins have a larger diameter of, e.g., 0.4 mm as against the outer cylinder walls of the cap.

In certain embodiments according to the present invention, the valve body is built in the cap in a pre-stressed, force- and form interlocking and axially free-of-play manner.

Some or all embodiments according to the present invention may exhibit one or several of the aforementioned or below stated advantages.

In some embodiments according to the present invention, the activation, i.e., the check or non-return function is advantageously maintained also after the removal of the disposable. In this way, the escaping of fluid, also during the removal at the three mentioned points, may be prevented by means of the remanently activated check valve according to the present invention. Hereby, two hose clamps and a user needed to actuate them are not required or can be spared. Furthermore, it is advantageously not required to have any closure sleeves in the substitute connector (see thereto, the reference numeral 41 in FIG. 1 of International Patent Publication No. WO 2010/121819 A1) and a thereto associated working stroke of the machine in order to ensure a protection against contamination caused by the escaping liquids.

The check valves according to the present invention may advantageously mobilize the required robustness against an early activation in the production prior to the sterilization.

In addition, embodiments according to the present invention may offer advantages in the automatic fabrication, the safe sterilization and the increase of the quality of the check valve functions. Large-pore drainage structures to smooth films and smooth injection molding walls and a low amount of wide-area component contacts contribute thereto, further, a safe continuance in the open initialization, i.e. in the first position, until the completion of the gas sterilization, low and defined changes in properties due to gas sterilization, in particular, of the pressure opening, the minimizing of changes of properties of the mounted check valves caused by mechanical, thermal or irradiation-induced load during the storage and transport which may influence the process of the safe and precise activation in line with the equipping process, preventing the so-far tolerated protrusion of the film-sided front/end surface of the check valves beyond the film plane of the cassette (check valves cause local dents in the film) for ensuring a safe producible film welding seam based on a continuously flat film mounted onto the cassette, more-tolerant-to-tolerance design of the individual parts and their interaction by both the mounting and interaction with the treatment machine at concurrently high reproducibility of the tightness, of the pressure opening and of the discharge pressure drop curve and therethrough a safe functioning also in the high-volume production and in many or aged treatment machines available in the market, increasing the reproducibility of the discharge pressure opening, reducing the pressure drop in the discharge area, i.e. minimizing the pressure drop at each volumetric flow discharge, flattening of the curve of the volumetric flow pressure drop discharge, i.e. minimizing the increase of the pressure drop with the increase of the volumetric flow discharge, increase of the fine and long-term intrusion tightness under/below the discharge opening pressure, in particular, tightness against air intrusion, reducing the sensibility against leakage by the presence of contamination particles and improving the capability of self-cleaning, further safe and tight sealing in the exclusion area up to the maximum pressure, and preventing vibration or swinging and noise emissions.

Further advantages are:
the low risk of malfunction after activation;

safe performance also at maximum possible axial activation hub (measured against the film) of ca. 1.2 mm, which is predetermined by the cassette construction and the blood treatment apparatus;

improving the characteristic value is achievable, as improved configuration and small tolerances in components are, in this regard, achievable;

reversible activation is feasible during the production up to the functional testing;

no problem of the uneven injection-molding production with welding lines and therewith associated leakage;

sufficient, constant geometry after the vapor sterilization;

insignificant relaxation during the prestressed, activated position, which may reduce the valve prestressing or bias during use and in this way may have an effect on the parameter pressure opening and outflow pressure drop;

high tolerance bridging through material combination elastomer-thermoplastic and through knobs geometry, therefore a low-cost and safe production with large permissible variations or dimension tolerances;

safe axial power limitation due to being completely made from elastomer and being axially flexible through the bottom ribs;

good gas sterilizability through broad drainages and little compressing surfaces between valve body and valve seat through convexity of the clamping aligning ribs;

triggering pressure and pressure volumetric flow characteristics depend only on the selected material, the selected wall thickness and diameters and of the production tolerance of the measurements and the properties of the material, however not on the size of the activation hubs provided the effective activation hub be within the planned range (here 1.2 to 1.8 mm);

no undercuts and therewith no deformation problems by assembling the valve seat in the cassette;

furthermore a one-piece check valve with low risk of malfunction after activation;

simple assembly procedures good tolerance compensation against axial assembly tiltings;

uncoupling of the activation path, and therewith the valve prestressing or bias, of the machine tolerances;

noticeable improvement of the reproducibility of pressure openings and characteristic line of the pressure volume flow;

flattening of the characteristic line of the pressure volumetric flow the result of which is that lower pressure loss and lower opening pressure configuration are realizable;

ergonomic advantages through little injection actuating power by infusion of medication;

lower haemolysis when used utilized for or during blood infusion;

simple preassembly of the valve in the cap or cap at higher reproducibility of the radial alignment;

possibility to test the functionality of the valve arrangement by the production after mounting of the cassette film;

due to the bellow shape of the valve, a more linear spring characteristic line is realizable as/than with, e.g., the simple mushroom shape;

the sealing ring area of the valve elements is not disposed or positioned, with regard to the flow relations in preferred production as LSR injection molding (Liquid Silicon Rubber), at the end of the flow path (such as with simple mushroom shape) and therefore avoiding weld lines and therewith the welding defects which cause leakage;

very little material and low cost are required for the manufacturing or execution of the check valve (0.5 Euro cent);

easily automatable mounting of the valve arrangement in a free rotatory positioning manner;

good aligning performance of the sealing ring area;

safe avoidance of friction between valve and cap by activation and flow through;

axially, particularly, very compact valve arrangement with therewith-associated reducible flow dead spaces;

advantages in characteristics and tolerance performance like the other prestressed valve designs with cap;

gas-open initial position for ensuring safe gas sterilization performance;

robust initial position with higher release expansive force despite little activation path;

avoiding the escape of unwanted fluids, after the removal, through remanent activation;

safe remanent activation, during equipping with safe position preservation after removal through friction closure and large prestressing or bias of the activation valve;

hard enveloping cap encapsulates the soft valve against mechanical interventions or modifications;

new mechanism of snap-in tongue or pin-wedge-diameter landing for robust gas-open initial position and defined strong release expansive force;

extreme low activation path in relation to the valve diameter allows a machine-sided passive activation actuator by flat film initial position and low film stress or stressing;

new cant-safe activation or plane bearing mechanism, consciously taking into account the possible tilting in the regular shift manner;

special geometrical arrangement with reduction of the tolerance chain;

decreased tolerances through precise producible compact function-determined geometries;

reduction of the valve tolerances through mutual geometrical calibration of assembled components;

utilizing the thermal and temporal material stress reduction through sterilization and storage so that the activation expansive force is calibrated and reduced during treatment, however, it is to be set as high as possible during valve production;

uncoupling of the positioning tolerance of the valve to the valve seat from the initiated forces and paths of the treatment machine by means of interposition of the cap;

principle of prestressing or bias leads to greater prestress path and as a result the characteristics of a valve are more exact, exhibit lower pressure drop and are therefore also more taken-care-of treatment fluid (lower shear stress at same volumetric flow);

conical or spherical segment-shaped valve sealing seats lead less-tolerance valve characteristics, an increase of sealing at a non-operating step, to a capability of self-cleaning, higher sealing capability in case of impurity and material defects;

overall stiffness and local barbs and soft valve sealing ring geometry lead to higher sealing capability in case of impurity and material defects;

extremely cost-effective production of the individual component through on-off de-molding principle, minimized injection molding cycle time through equal wall thickness and less material consumption and, due to less elongation, a possible application of a film containing relatively little elastomer and therefore being cost-effective;

specifically more exact component geometry through rotationally-symmetrical stiff geometry and central gating;

no or hardly any air bubbles and weld line in the sealing ring zone through geometrical shifting away from the end of the flow path;

complete automatable production and testing concept which is conceptually included by taken into consideration all parts and handling tolerances with specially good characteristics of self-aligning and freedom of rotation positioning of all components;

complete fluidic testing of the valve in a finished, equipped state is realizable through reversible activation;

self-compensatory characteristic against relaxation in the characteristic line during use;

utilizing deformation characteristics specifically of rolling bellows for the flattening of pressure loss-volumetric flow characteristic line;

optimized drainage and sterilization patterns of the thermoplastic cap as functional improvement in comparison with patterns of the elastomer valve components;

conical alignment with a large opening angle, patterns in axial directions, matt erodings and axial support zones by the cap for optimized collaborate functionality with the soft sticky elastomer material of the valve;

possibility to set the opening pressure, because of higher reproducibility at same safety level, at a lower value, hence, more ergonomic spraying of treatment fluid, lower material-caring pressure level from supply or feeding pumps or less haemolysis by blood return through the check valve;

many and/or uneven-numbered, equal division of through openings and snap-in tongues or pins, which enables low-pressure-drop and equal flow through of the valve arrangement, without rotary orientation also by several fluid channels going out of valve seats and having good centering property;

technically functional use of the de-molding partition line for functionalities of the vale such as friction by axial shifting and canting-insensitive tilting with omission of the usually mostly existing necessity of producing the injection molding in a burr-free manner;

extensive activation ring surface made of hard thermoplastic material reduces the activation pressing stress on the activation hump of the machine and reduces inaccuracy of the activation path transition though elastical flexibility onto machines and valve components;

advantageous form design in focus and shape symmetry of cap and valve for the safe vibration requirements and orientation sorting by provision and pre-positioning of parts;

conical, round, central geometries of cap and valve allow a suction process and precise further and end centering with tubular vacuum grabs and round reception bores;

possibility to apply or implement a specially simple and passively effective activation device on the machine side requiring neutral costs for integrating a progressively operating activation hump springing in the hermetically encapsulated actuator-sensor-mat;

possibility to apply a likewise encapsulated, inserted activation device, discretely structured with technical springs, in the area behind the actuator-sensor-mat;

possibility to apply an actively drivable activation device encapsulated behind the actuator-sensor-mat with the possibility to be able to perform a complete functionality test of the valve arrangement prior to beginning with the treatment and to further be able to procedurally use, apart from the check valve function, also the function of double-sided open flow paths;

use of the differences of static friction and sliding friction in the activation mechanism of the cap in order to maintain a high activation expansive force with low further shifting force after overcoming the snap-in barrier;

use of convex or pointed knobs or shaft structures in the actuator-sensor-mat, in order to maintain a progressive force path characteristic line, which may connect a high activation expansive force with low residual force in the activated position;

valve opening occurring merely through bending processes in the elastomer valve, therefore an extensive drop of hysteresis and variations in reproducibility;

low clogging tendency through equal and complete lifting of the sealing ring when the valve in being opened while avoiding the flow dead zones and fluid dwell times at the non-lifting zones of the sealing ring;

low sensitivity to the causing of vibrations and noises or sounds, as the valve sealing ring lifts up equally and therefore substantially allowing only a basic mode of vibration.

In certain embodiments according to the present invention, the valve injection molding may advantageously be manufactured according to a low-priced on-off conception, wherein the required number of molding post, due to the longer specific cycle time for the cross linking of fluid silicons, is to be set higher up than by snap-in molding to about factor 2. It is possible to manufacture the valve in an extremely inexpensive manner through the simple and substantially rotationally symmetrical shape, through the plane, sealable, mismatch in mold and mold-parting-line-uncritical mold release at the bottom surrounding angle of the support ring and through the very small construction volume of ca. 110 mm^3. Due to fact that LSR components are normally the ones which are swept, most economically, out of the ejector-sided mold cavity due to the lateral attached rotary spatula, the valve is therefore designed in the optimal producibility and thereby makes use of the centering cone as a central feed point and, during the de-molding process, as sweeping nipple which protrudes out of the ejector-sided mold half. The check-valve designs of the functional device according to the present invention comprise the characteristic to be centrally molded and substantially rotationally symmetric which is advantageous for a warping or deformation-low shape of mold.

It is also advantageous that no large portion of its volume is arranged in the vicinity of the center (mushroom base area), while the portion of its volume near the sealing ring is relatively big and thereby it is not positioned in the immediate vicinity to the end of the flow path and to the mold release. The result of which is that the liquid injection molding in the process of filling of the sealing ring area does not take place already shortly before completion of the mold filling, the flow speed does not come to a standstill and air bubbles and weld seams are not further moved. In this manner, one does not have the problem that air voids or air pockets or entrapped air and weld seams and the therewith related geometrical inaccuracy at the surface are of all things obtained at the sealing ring and therefore reducing the sealing capability of the valve at the ring-shaped area of the contact with the sealing surface at the valve seat.

The check valve of the functional device according to the present invention, comprises in certain embodiments according to the present invention a shape which specially supports in its production the filling of the mold form: The centrally injected liquid elastomer initially collides against the support front end and is abruptly diverted or redirected into the thin-walled wave form of the spring membrane, it flows after renewed diversion or redirection through the sealing ring and further to the relatively voluminous support ring where the mold release with the ventilation and flow path ends are positioned. The sealing ring is therefore flown in with homogenized injection molding compound by relatively high flow speed and therewith the air voids and weld seams (partially frozen or solidified flow fronts) are further moved. Hence, one obtains a sealing ring with particularly more accurate and, for sealing, more suitable surface.

Due to the low stiffness of elastomeric components (herein about 40 to 70 Shore A) and in relation to the relatively high stiffness of the cap, there are in certain embodiments according to the present invention structurings, which are advantageously arranged in the cap components rather than in the valve components, for the accessibility of sterilization gases, for the air exhaustion or outflow and friction reduction by the assembly. One needs less deep structures in the cap, in order to maintain equally large continuously-open structures in a pressed and built-up state, than by arranging corresponding structures in the valve components. This is the result of the fact that the raised and the impressed structures are flattened out at the elastomer and therefore the undesired direct surface contact between the thermoplastic and the elastomeric components increase, while at the same time, the desired gas-conducting drainage grooves decrease in cross section. In addition, it is beneficial for the error-free production of the surface of the elastomeric parts when there are no difficult-to-squeeze out and difficult-to-ventilate structures, which is not to be considered in the production of the cap due to the fact that, in this case, small defects in the surface have no influence on the function.

Further possible advantages relate to particularly the tolerance optimization. In details:

1. By the prestressing or bias of the valve in the snap-in-cap, the valve adjusts to the snap-in-cap in several axial dimensions and it orients itself towards the more rigid and more accurately producible snap-in-cap also according to the axial run-out, radial spacing and axial alignment, whereby already several dimension tolerances of the valve become less relevant or even meaningless already.
2. Due to the fact that for the position "activated", the only matter of importance is that the cap, with its lower ring front end, flatly lies at the valve seat ring support, it is meaningless which path the actuator-sensor-plate of the treatment machine takes for the shifting of the cap into the activation hump, as long as the path is at least big enough so that the cap comes to lay planar. This is a distinctive difference to most of the, softly designed, known valve designs with proportional dependence of the activation path of the valve on the activation path of the machine. One obtains an approximately complete decoupling between the activations paths of the valve and the activation actuator of the machine.
3. Due to the fact that the cap is a component which is an order of magnitude stiffer than the elastomeric valve body, the axial self-deformations, under the introduced activation forces, are accordingly less. Hereby, the axial position uncertainty of the aligning cone of cap and therewith the central area of the valve drop to about more than an order of magnitude (0.02 to 0.04 mm) than with the previous designs with no cap, by which the penetration depth and axial force of the activation hump of the treatment machine had taken direct influence on the axial shifting of the central area of the valve and therewith the operational prestressing or bias of the activated valve. Thus, one obtains an approximately complete decoupling between the prestress forces of the valve in the activation position and the activation forces of the activation actuator of the machine.
4. The geometrically mechanical chain of the influencing tolerances includes only a small part of the previous dimensions, namely the dimensions of the valve and the, immediately around it, topologies of the valve seat and cap interior which are involved in the valve clamping. As all these topologies have only small dimensions in the range of 0.4 to 3.6 mm in Z-direction, the achievable production tolerances of the injection molding topologies are accordingly small and are in the range of less than +/−0.03 mm. One obtains therefore significant shortening of the tolerance chains and at the same time narrower single tolerances.
5. By the plane contact of both ring surfaces mentioned supra, under a continuous residual force of typically 5 to 20 N, the axial run-out deviations of both ring surfaces mutually reduce themselves as they mutually level themselves in an elastic-plastic manner. This is a typical process in case the axial compression injection molding components, which are basically effected by the angel deformations, are exposed against pointing counter surfaces. One obtains such an increase in accuracy by mutual design optimization of the installed components.
6. The spring membrane of the valve has a similar shape to a rolling bellows The design-change processes by the axial deflection or modulation of the valve are not to be equated with a genuine rolling bellows, because the cylindrical rolling or turning surfaces for the prevention of movement friction are missing. The design similar to rolling bellows has specific advantages compared to a flat spring membrane:
6a. By the same axial prestressing or bias, the angle flexibility at the level of the sealing ring is clearly increased, which leads to a more even or steady sealing compression and therefore to a narrower spreading of the opening pressure by radial and angular misalignment or displacement of the symmetry axis of the valve to a symmetry axis of the valve seat.
6b. Due to the relative stiffness of the support ring in connection with the mostly vertical wall section between support ring and sealing ring, a generally-specific stiff sealing ring zone results or arises, which is shifted through the rolling membrane, rather as a whole, and thus adjusting to the sealing ring of the valve seat when shifted in an angular radial and axial manner. Locally, i.e. with reference to the local compression of the elastomeric valve sealing ring onto the hard valve seat sealing ring, the tightening adjustment of both surfaces is therefore intensified or reinforced such that the valve sealing ring builds up relative sharp edges (pointed elements of a sealing compression combination) and it locally flattens out above its low hardness of about 30 to 70 Shore A at the valve seat sealing ring. Thereby, high surface compression locally arises which represents the decisive criteria of a locally effective sealing bridging of local irregularities of both sealing surfaces or foreign objects locally present in the sealing zone. In the case of most of the so far proposed valve designs, the valve sealing ring zone is thin-walled and generally or as a whole a little stiffer. Thereby, the irregularities and foreign objects lead to a general deformation of the sealing ring zone and not to a local bridging and encapsulation, hence, the sealing effect is reduced by local spacing or gab formation. Therefore, the valve according to the present invention seals in a more reproducible manner and in a better way under the influence of local surface defects and foreign objects present in the sealing zone.

6c. The design similar to a rolling bellows also has an influence on the linearity of the spring property of the axial shifting of the sealing ring. Starting from a certain axial minimum deflection, rolling bellows comprise a constantly continuing or even declining force at any further deflection. The minimum deflection is then reached when the bending stress condition does not change anymore, i.e. the rolling bellow has taken a similar constantly continuing form. The thereto required deflection axial path is by a genuine rolling bellows about 3 to 5 times higher than the strength of the rolling bellows. Through the prestressing or bias of the cap valves, such a path, may be impressed. This is not possible with pre-stressing-free designs due to the limited activation path of 0.8, because only ca. 0.4 mm remain from this path, which is already less than the present rolling bellows strength, for the axial prestressing or bias after having deducted the minimum sterilization slot and the addable up tolerances. The typical rolling-bellows property of limiting the axial force enables that the valves are designed such that the force path characteristic line approximately horizontally proceeds and therewith the tolerance sensitivity of the opening pressure and of the flow resistance may still be reduced one more time.

7. Through the prestressing or bias of the valve in the cap and the release of this prestressing or bias and other prestressing or bias in the second or activated position, the new valve may be prestressed with a clearly higher path than valves without cap and without prestressing or bias; therefore, more flexible spring membrane geometries, having flatter spring characteristic line, may be utilized in the second position and therewith leading, by same activation path irregularities, to smaller uncertainties of the opening pressure like the pressure drops and irregularities in pressure drops.

8. However due to the fact that the cap conception, as explained supra, leads to an extensive decoupling of the valve from the actuator of the machine and moreover the geometrical tolerances will decrease by skillful component arrangement or lay out, the tolerances of the above-mentioned characteristic line values are further reduced.

9. Through the tolerance-low second, activated position in connection with the flatter valve spring characteristic line and the stronger prestressing or bias, a particularly safe remanent activation of the valve, after the removal of the disposable, is reached. The cap, which is frictionally retained in the activated position, does not actuate itself when an excess pressure of up to 0.6 bar develops or arises in the disposable. In practice, this pressure cannot occur under regular removal conditions as the gas compliance of the emptied or drained disposable does not permit the development of such pressure.

The wedge effect and the higher sealing compression are accompanied in certain embodiments according to the present invention by a higher self-cleaning effect of the valve during opening and closing, a particularly useful property, because, due to the wedged-shaped arrangement of the valve seat sealing ring, normal and tangential movement overlap during the lifting off of the valve there, whereby the tangential movement causes or brings forth the cleaning effect, however also, up to the lifting off of the valve, the here desired hysteresis effect (higher opening pressure) after a longer-lasting sealing time. The preferred conical valve sealing seat has, as already further indicated above, more favorable angle tolerance properties than a flat valve seat, as it comes closer to resemble a shape of ball scraper. In an ideal embodiment, the valve sealing seat may take the form of a ball scraper, which is impressed by exactly the radius that corresponds to a tolerance-limited pendulum inclination of the valve axis to the valve seat axis: In this case, the valve sealing ring requires only a minimum of general elastical deformation in order to adjust itself to the valve sealing seat ring. However, the dimensioning of the prestressing or bias relationships is more difficult, as the cone walls do not have any constant increase any further.

Attempts or experiments with air and different fluids have shown that the valve in certain embodiments according to the present invention, in the provided volumetric flow area, does not create any audible noises or measurable pressure vibrations. By radiography or X-ray photograph with continuous flow through of air, it was possible to observe a regular opening. It is associated therewith that the valve design in certain embodiments according to the present invention has only a slight tendency for clogging or loading through clinging particle, in particular with regard to clinging clotting blood, as no seal-remaining sections are left, in which the blood flow comes to a halt or stop. The conical design forms a flow channel which most continuously directs the specified geometrical course of inflow from inside-down to top-outside. The outcome of this is also a less flow loss of the flowing of the housing (due to less abrupt change of direction of flow) and an improved ventilation possibility of the main flow path (due to higher average flow velocity)

By very high volumetric flow outside of the specified areas, the interior arched capping of the cap acts, in certain embodiments according to the present invention, as movement stop for the valve retaining ring which is being lifted by the fluid. The flat movement stop is geometrically designed in a way that no possibilities of deadlock of the valve onto the cap arch may arise. With the arising typical barrier or sealing pressures up to about 1.5 bar and within the specified volumetric flow range from 0 to 600 ml/min, the valve opens by itself through bending movements, whereby the inner material portion of the valve is kept almost free of play between centering cone and stop end and the retaining ring is spaced in all spatial directions without touching or contact distance to cap and valve seat. With drop of sliding movements (e.g. by check valves with re-locatable balls), the characteristic line is highly reproducible and almost hysteresis-free. By normal barrier or sealing pressures up to 2.5 bar, the sealing ring area of the valve continuously comes to sit more tightly to the sealing cone of the valve seat and reinforcing or intensifying the sealing effect. By extreme barrier or sealing pressures up to ca. 5 bar, the spring membrane area of the valve buckles to the inside and returns back into the correct initial position or state by pressure withdrawal. By normal and extreme barrier or sealing pressures, the centering protrusion in the center of the valve seat prevents an axial movement or shifting and an axial-radial misalignment of the valve position. In addition, it diminishes the flow space and, hence, contributes to consistent flow velocities.

By longer phases of higher volumetric flows, the valve relaxes some millibar towards the decreasing flow resistance, a typical reaction of elastomeric material. Among or under these materials, the silicon rubber has a significant place due to especially lower relaxation. However due to the fact that also the cap relaxes, through the persisting residual axial force onto the cap, towards the valve seat base, a compensating effect takes place as this relaxation direction is consistent with the increasing prestressing or bias direction. In this way, the valve design having a cap offers lower relaxation of the pressure volumetric flow characteristic line through the compensating mounting arrangement. Throughout suitable series of tests or experiments, the geometrical configuration, in particular of the cone seat area of the cap, can be optimized, taking into consideration the component or element tolerance of disposable and machine, the treatment temperatures and times and the wear and tear operations of the machine, so that an optimal middle mutual compensation of the relaxations of valve and cap is determined and implemented.

The tightness of the equipped cassette disposable in the place where it is intended to be located at or in, has proven to be so unreliable that a closure sleeve (having the corresponding seal function), in particular at the substitute connector, can be omitted by series disposable, see here the reference numeral 41 in FIG. 1 of International Patent Publication No. WO 2010/121819 A1. This is accompanied by further simplification of the machine-sided actuator-sensor-coupling mechanism, which does not need to use a hub for the sealing activation of the closure sleeve anymore and at the same time performing more economically and more reliably.

The present invention shall be exemplary explained with reference to the appended drawings or illustrations, in which identical reference numerals refer to same or identical elements. In the partially strongly simplified figures, the following applies:

FIG. 1d shows an enlargement of FIG. 1c;

DETAILED DESCRIPTION

Figure 1A:
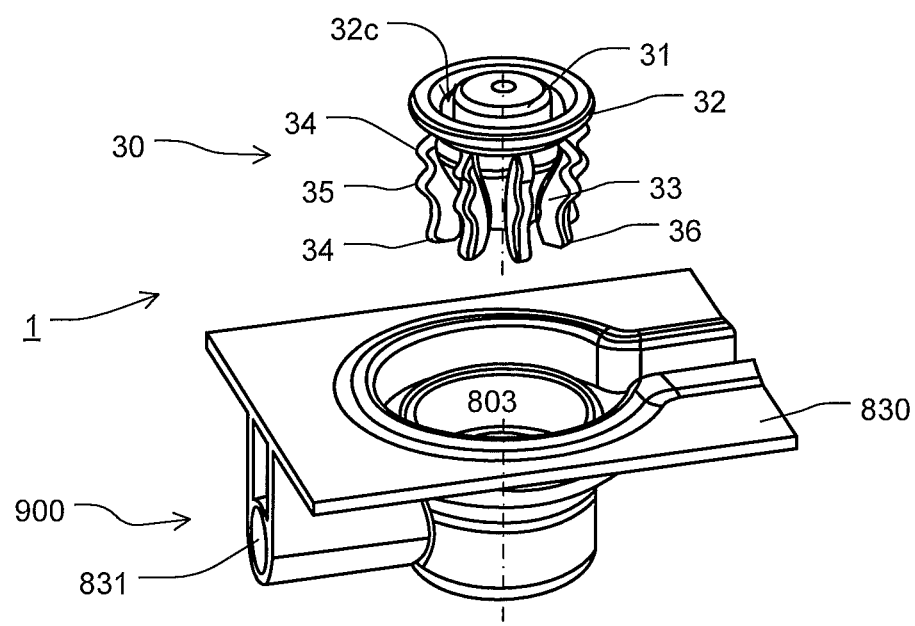
FIG. 1a to 1c show the check valve arrangement in a first exemplary embodiment according to the present invention.
Figure 1B:
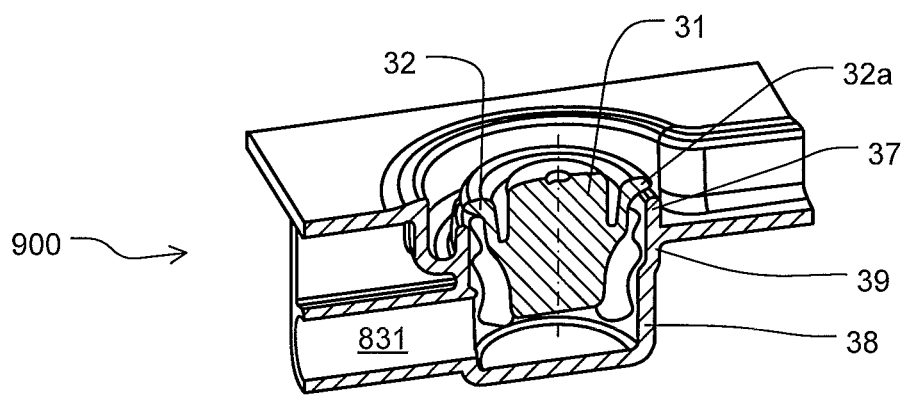
Figure 1C:
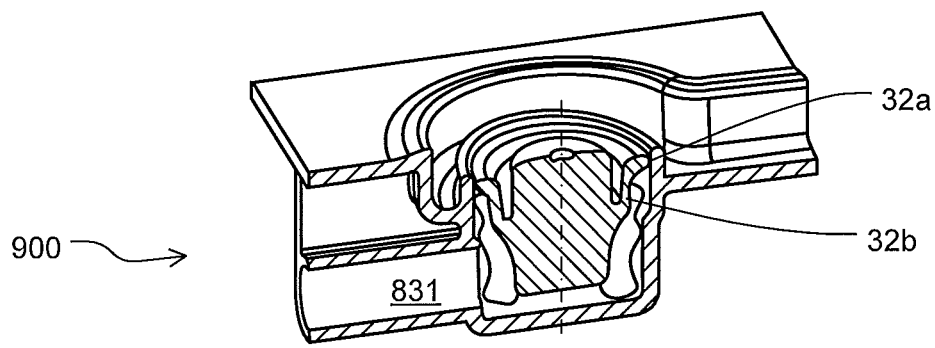

The FIG. 1a to 1c show the check valve arrangement 1 in a first, exemplary embodiment of the functional device according to the present invention.

FIG. 1a shows the valve arrangement 1 in an exploded view, FIG. 1b in first position, i.e. in the non-activated, open initial position, and FIG. 1c in second position, i.e. the "remanent" (i.e. "continuous" or "permanent") activated check valve position.

A one-piece valve body 30 is made up of silicon rubber. A centrically positioned cylinder or section of the valve body 30, denoted here as core cylinder 31, serves, with its front end facing the film, as a sufficiently stiff transmission element for the axial activation hub which is to be introduced, over the cassette film and the activation actuator of the machine (in short also actuator, which is not represented or illustrated here, see however FIG. 6f). A radial sealing bar 32, for example cup-shaped, is peripheral (i.e. in a closed contour or with a closed circumference). Ribs, here also denoted as guiding clamping drainage ribs 33, which serve for guiding, clamping and draining are preferably connected with an outer area of the core cylinder 31 in an equal or uneven division and in a preferred number of more than 2. The guiding clamping drainage ribs 33 centrally hold the valve body 30, via a slightly radial jamming and under bridging the radial measurement size or dimension tolerances of valve body 30 and valve seat 803 of the hard body 830 of the cassette 900, in a sealing cylinder 37 and in a guiding cylinder 38 (see FIG. 1b) of the valve seat 803 of the cassette 900. Thereby the guiding clamping drainage ribs 33, for example by means of optional clamping knobs 34 which may be axially placed on one and the same guiding clamping drainage ribs 33, also prevent a tilting of the valve body 30.

Adjacent guiding clamping drainage ribs 33 are not in contact with each other in the example of FIG. 1a to 1d.

Through the knobs geometry, i.e. through the limited axial extension and the convexity, tolerances-bridging high radial measurement overlapping with the adjacent cylinder 37 and 38, which have different large diameters, wherein the area of the diameter transition or step or level is denoted as snap-in step 39, may be achieved by defined friction-closure centering and axial fixation of the valve body 30.

The reference numeral 32c denotes a peripheral or closed slot which is described with regard to FIG. 1d.

Tests have shown that the slip-stick effects in comparison with axially continuous ribs, i.e. ribs without projecting clamping guiding knobs 34, turn out to be lower and therefore the possibility of tiltings during the mounting and during the start of the activation hub is advantageously reduced.

FIG. 1 shows the first position, the flow-open basic position, in section: The valve body 30 is fixed at the snap-in step 39 in the flow-open basic or initial position (first position) both through friction closure of the clamping guiding knobs 34 as well as through the arrangement of knobs, here also denoted as clamping snap-in knobs 35, which project over or beyond the clamping guiding knobs 34. In this position, the radial sealing bar 32 is in an axial disengagement to the sealing cylinder 37, and there is a flow-open ring volume (a sterilization slot). Only by applying a minimum activating force (preferred is 20 to 40 N), axially towards the front end of the core cylinder 31, an axial shifting movement starts as the sum of the holding force of the clamping guiding knobs 34 and the resulting radial, effective deformation force upon the clamping-snap-in knobs 35, towards the interior of the clamping snap-in knobs 35, exceeds the preset limit. In doing so, the protection against unintended activation during the production of the cassette 900 is ensured.

In the bottom area of the valve body 30—and only preferably at a lower end of its guiding clamping drainage ribs 33—provided drainage bottom ribs 36 limit the effect of the activation hub in axial direction. They may further ensure, together with some or all other ribs, the equal de-aeration and flow properties of the valve body as well as the safe sterilizability by means of gas.

FIG. 1c shows the activated check valve position in section: The thin-walled cup envelope 32b and the peripheral radial sealing bar 32 with a somewhat thicker wall having a tapered sealing edge 32a form together with the sealing cylinder 37 of the valve seat 803 of the cassette 900 a check-valve sealing system following the running of the activation hub. Thereby, the peripheral sealing edge 32a of the elastomer valve body 30 and under radial prestressing or bias is positioned on the sealing cylinder 37 sealing the film-sided fluid space against the connector-sided fluid space, i.e. against the space 831, out of which fluid from the machine-sided connector may flow towards the valve 30.

In case the connector-sided fluid space exceeds a defined opening pressure (for example of 180 mbar) against the film-sided fluid space, then the radially inwardly effecting fluid force upon a cup envelope 32b increases and two elastical deformations take place, namely a diameter reduction of the cup envelope 32b and the radial sealing bar 32 and a radial buckling or creasing of the radial sealing bar 32. In this manner, flow lumina open up at one or several points between the sealing edge 32a and the sealing cylinder 37.

In case of a prevailing vacuum or negative pressure, which is lower than that of the set pressure, balanced pressure or an excess pressure in the fluid system of the cassette 900 on the film side (and therewith on the sides of the channels and chambers), the film-sided fluid space remains then sealed against the connector-sided fluid space. In the case of an excess pressure, the application of pressure effects radially and outwardly upon the cup envelope 32b and in a tight-closure enforced manner upon the sealing edge 32a.

The FIG. 1a to 1c show therefore a one-piece valve body or an insertion of the check valve, made of elastomer, from the radially sealing type, into the functional device according to the present invention.

In further exemplary embodiments, the check valve arrangement 1, shown in FIG. 1a-1c, may however comprise an additional plug component. In this way, the core cylinder 31 may be provided with a blind hole on the side of the film or the connector, which is refilled via a plug provided with drainage ribs made of thermoplastic (the same or similar to the thermoplastic material of the cassette). This plug reduces material usage with elastomeric valve body and increases the axial stiffness of the core cylinder 31. In this way, the required activation axial hub can be slightly decreased.

FIG. 1d shows an enlargement of FIG. 1c. One can recognize the cup envelope 32b in section.

The cup envelope 32b may be understood as, for example, conical or cylindrical wall which extends in an open-closed direction of the valve body 30.

The cup envelope 32b may be understood as peripheral wall which at least peripherally, i.e. in a closed form, surrounds the core cylinder 31. Thereby, a likewise peripheral slot 32c may be provided between the wall of the cup envelope 32c and the outer zone on the side (envelope surface) of the core cylinder 31. The slot may have a slot base 32d in which the core cylinder 31 or central sections thereof are merged into the cup envelope 32b.

Figure 2A:
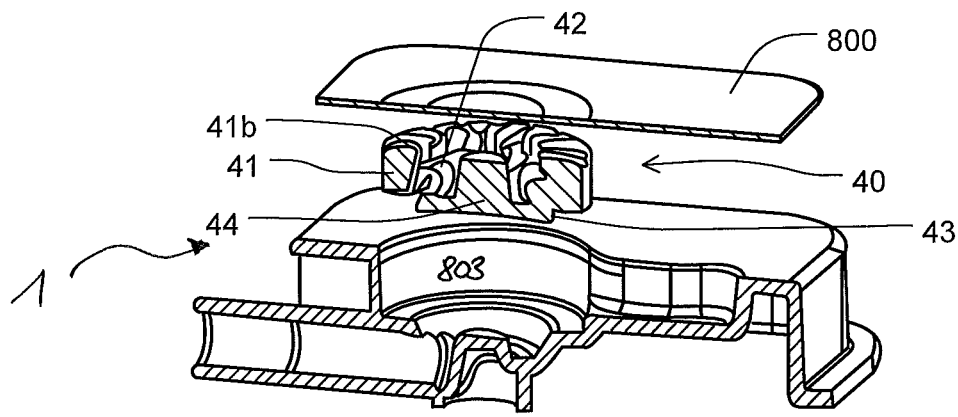
FIGS. 2a to 2d show the one-piece design of a further embodiment according to the present invention having a one-piece, claw-shaped check valve arrangement.
Figure 2B:
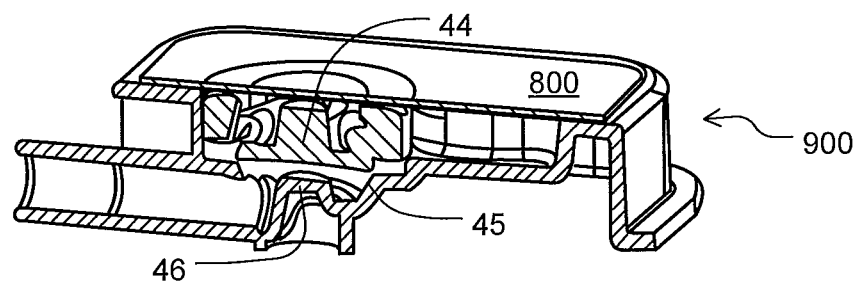
Figure 2C:
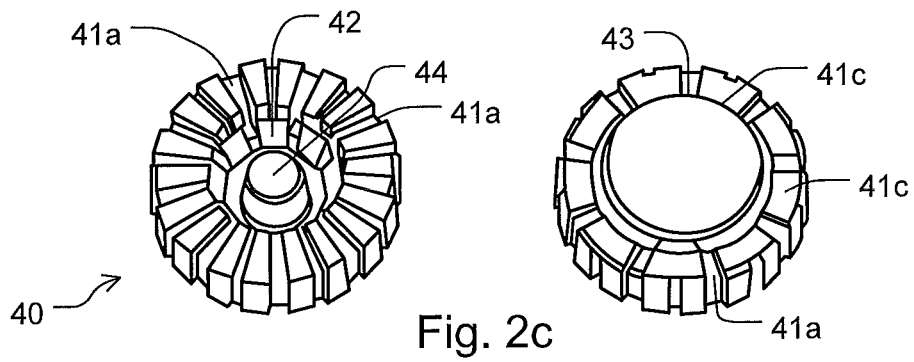
Figure 2D:
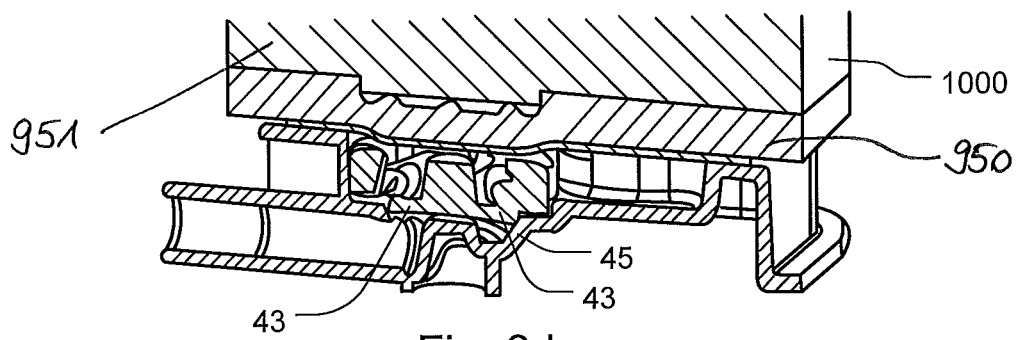

The FIGS. 2a to 2d show the one-piece design of a further embodiment according to the present invention with a one-piece claw-shaped check valve arrangement 1, in an exploded illustration (see FIG. 2a), in a first position ("initial", FIG. 2b) in perspective view from top and bottom (FIG. 2c) as well as in a second position ("activated", FIG. 2d).

A valve body 40 is made up from elastomeric material, preferably from silicon rubber. It is preferably designed such that it may be produced by cost-effective open-closed injection molding.

A ring section, denoted herein as positioning ring 41, comprise peripheral drainage structures 41a which, in a mounted state, ensure the accessibility for sterilizing gas. An upper ring front end surface 41b of the positioning ring 41, in line with the illustration of FIG. 2a, points towards the film 800 of the cassette 900. In the first position of FIG. 2b, this surface sits substantially completely or at least in section preferably flush or leveled with the film 800 or with the cassette edge at/on which the film 800 is hung up or welded, whereby a friction plug-in assembly with axial movement stop results. An outer envelope surface of the positioning ring 41 comprises a larger diameter than the associated recess through opening in the cassette 900. Through the diameter differences, the material hardness and/or the design of the drainage structures which may have contact with the interior diameter of the recess through opening, the retention force caused by friction arises in the cassette, thus, maintaining the valve of FIGS. 2a to 2d in the second position. This shall be set in a range, for example, of 20 to 30 N.

The upper ring front end surface 41b serves by the activation in the dialysis machine 1000 for the introduction of the activation force (larger than, e.g., 20 to 30 N) or the activation path of ca. 1.1 to 1.4 mm. Through the compact design of the geometry of the positioning ring 41, an axial, rather stiff ring body which "transmits" the introduced axial path by mounting and by activation more accurately than an elastomeric plunger which is centrally arranged and which has a diameter like for example the embodiment of FIG. 1 according to the present invention. Hence, there is somewhat less need for gross activation path by machine 1000 and film 800.

A lower ring front end surface 41c serves as a movement stop and therewith "activating" the calibration of the pressure opening and the outlet characteristic line in the second position.

A section, which is herein denoted as outlet ring zone 42, consists of single spiral loop-shaped single bars having slots in between or comprises such ones. The outlet ring zone 42 serves for the fluid outlet into the position "activated", holds the valve core in the set position and builds an axially springy and tilting-position compensating support structure.

The exemplary, mushroom-shaped valve core comprises a stiffer core area 44 which serves, in both axial movement directions, as a movement stop against the film 800 and against the cassette-sided plunger 46. These stops are only touched when the determined pressure and volume flow area is abandoned.

The sealing ring zone 43 of the valve 40 which is exemplary designed as peripheral lip or peripheral edge, comprises in the first position a ring slot of, purely exemplary, ca 0.4 mm to a conical sealing seat 45 of the body of the cassette 900. This contributes in that the gas sterilization is reliably possible. On the other hand, the sealing ring zone 43—for example under minimum presetting of ca. 0.4 mm—seals against a conical sealing seat 45 of the body of the cassette 900. One can execute the type of sealing also as axial sealing with only a slight geometrical modification, which is encompassed as well by the present invention.

Thus, the FIGS. 2a to 2d show a one-piece valve body or core made of elastomer, which seals conically.

Figure 3A:
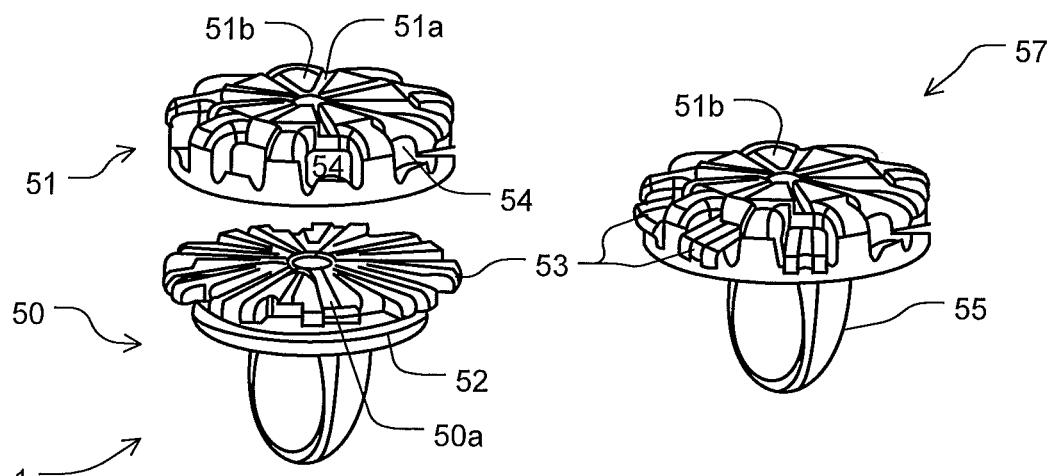
FIGS. 3a to 3c show a valve of a further exemplary embodiment having a cap made of thermoplastic.
Figure 3B:
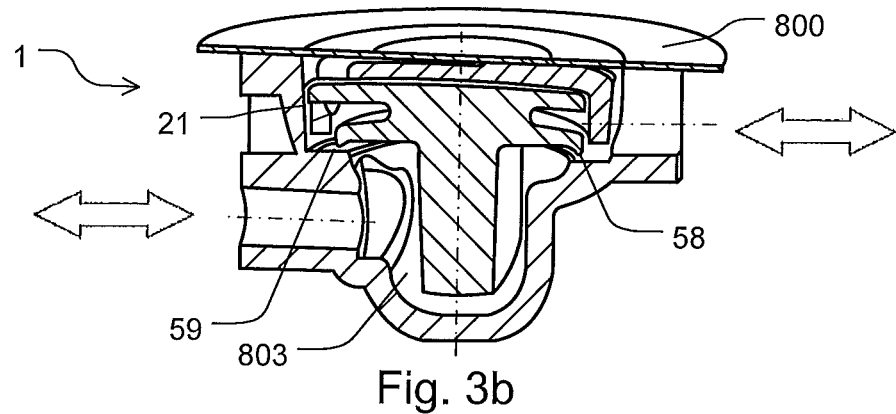
Figure 3C:
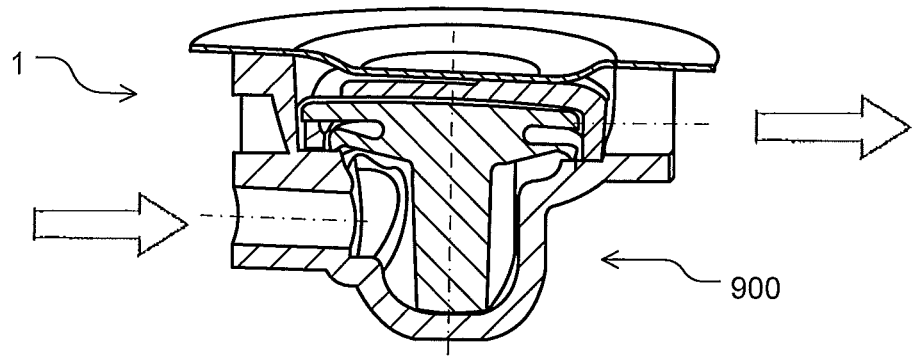

The FIGS. 3a to 3c show a further exemplary embodiment of a valve with a cap 51, preferably made of thermoplastic (preferably PP). FIG. 3a shows a valve body 50 and a cap 51 of the valve in an exploded illustration (left) and in an assembled state (right). FIG. 3b shows the valve in the first position ("initial"), FIG. 3c shows it in the second position ("activated").

The valve body 50 constitutes or forms together with the cap 51 the activation and retaining ring of the check valve or the check valve arrangement. After the pre-assembly of the valve body 50, which has a sealing ring 52, knobs 53 of the valve body 50 radially project or extend in the cap 51 out of through openings 54 of the cap 51 to the outside. Both valve body 50 and cap 51 optionally comprise drainage structures 50a and 51a for the optimal gas and/or vapor sterilizability. They are so geometrically matched to each other such that the valve body 50, with its activation front end and under lighter prestressing or bias, sits closely at the interior side of the activation front end of the cap 51.

The knobs 53 of the cap 51 or of the retention ring constitute or form together with the ribs 55 of the valve bottom, in which the sealing ring 52 in FIG. 3a exemplarily continues or at which the sealing ring 52 is hooked, a free-of-play holder or support of the valve arrangement 1 in the valve seat 803 of the cassette 900, which prevents an independent passing over of the valve out of the activated position into the initial position. The aforementioned components may jointly be denoted as retaining head 57.

Through the interaction with the step, denoted as diameter landing or change 21 in the retaining ring area of the cassette 900, within the cylinder-shaped section of the valve seat 803 of the cassette 900, the required shifting axial force in the valve seat 803 is, e.g., ca. 20 N in removing or demounting position and it is 30 N in activation position. This is enough on the one hand side for a sufficient and secure fixation in the gas-open first position during the production and on the other hand side for a low, required activation force in the treatment machine.

Through openings 54 and drainage structures 51a serve—preferably in connection with the convexity of the outer activation front/end surface 51b of the cap 51—also for the de-aeration possibility and the passage of treatment fluid through the valve arrangement 1.

The very stiff or in any case stiffer cap 51, in comparison with the valve body 50, allows the valve arrangement 1 to be axially mounted of about +/−0.2 mm right in the first position. For overcoming the sterilization slot of at least 0.2 mm and for building up a sufficient valve prestressing or bias, a nominal activation path of about 1 mm results. Due to the fact that only relatively low axial force is required for the shifting of the valve arrangement 1, which is maintained in friction-closure manner, the actuator-sensor assembly of the machine 1000 needs a protrusion of the activation nose of about 1.2 to 1.4 mm in order to achieve a secure activation, i.e. the second position. This is given or achieved when a ring front/end surface 58 of the valve body 50 comes into a large-surface contact with a ring front/end surface 59 of the valve seat 803 of the cassette 900. Even with a maximum activation force of 60 N, for example, from the machine onto the cap 51, the latter is axially dented about 0.05 mm only.

The specified arrows or double arrows in the FIGS. 3a to 3c show, respectively, in which direction the valve arrangement may be flown through: Due to the open, first position in FIG. 3b, they are both flow directions, i.e. both from left to right and vice versa. This does not apply in FIG. 3c which shows the activated, second position in which the valve arrangement acts as check valve. Here, the valve arrangement may only be flown through from left to right, provided there be sufficient pressure.

Hence, the FIGS. 3a to 3c show a two-piece valve arrangement or a two-piece valve seat made of elastomer or thermoplastic, which seals flatly, however it may conically seal by corresponding adjustment.

Figure 4A:
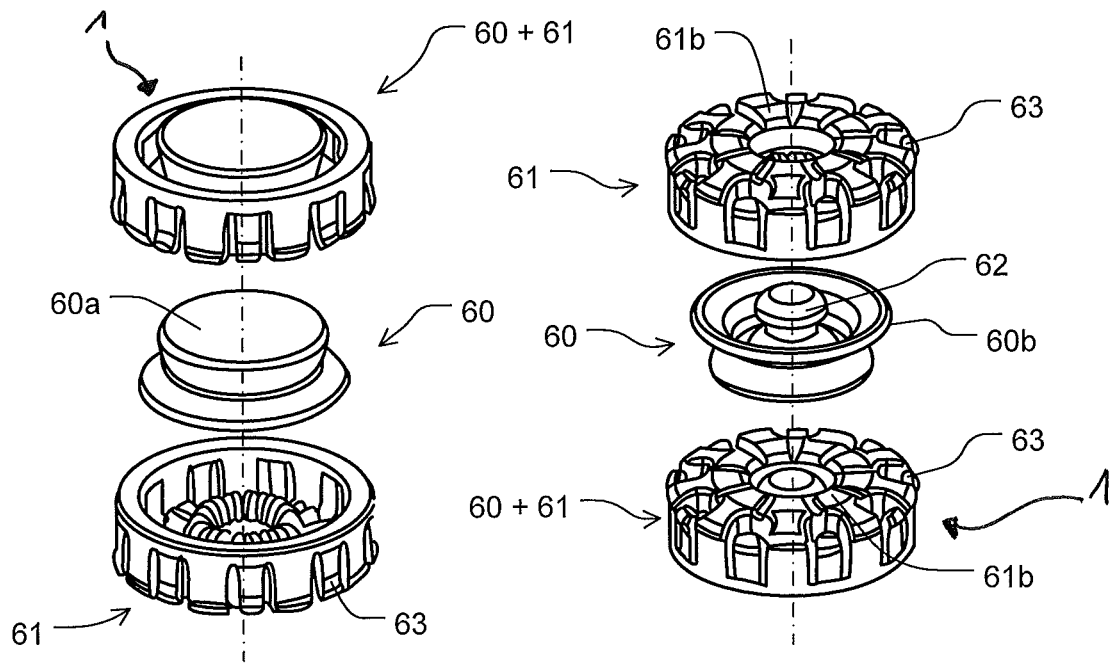
FIGS. 4a to 4c show a check valve arrangement in a further embodiment of the functional device according to the present invention.
Figure 4B:
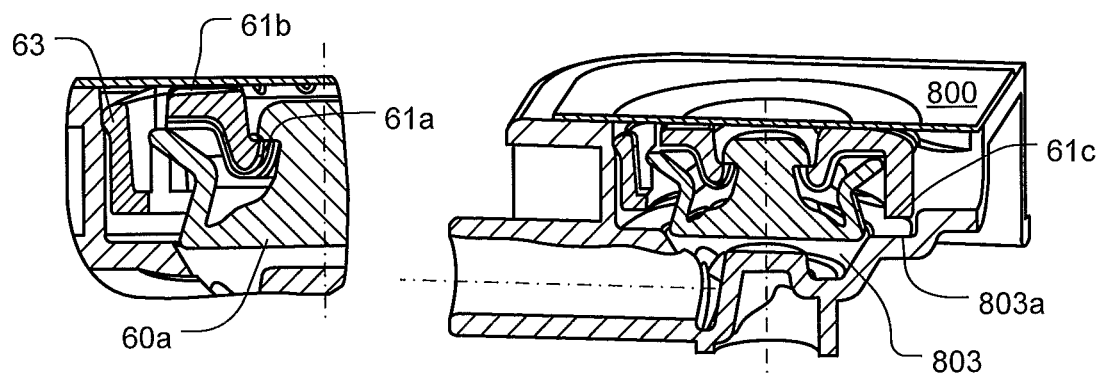
Figure 4C:
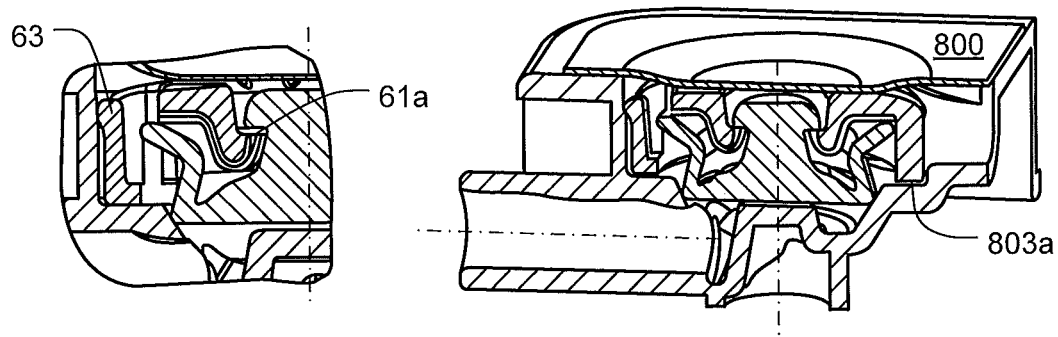

The FIGS. 4a to 4c show a check valve arrangement 1 of a further, exemplary embodiment according to the present invention. This is a two-piece valve arrangement, which conically seals, having a valve component made of elastomer (preferably silicon rubber) and a cap component made of thermoplastic (preferably PP), which are inserted in a valve seat 803. Thereby, the FIG. 4a shows the valve arrangement in an exploded illustration looked at from the bottom (left) or from the top, (right), wherein the illustrated top or bottom, and the respectively centrally illustrated, components are again assembled on the bottom or top (with reference to the drawing sheet). The FIG. 4b shows the valve arrangement 1 in so-called pre-stressed (expression shall be explained below), ("initial"), and the FIG. 4c shows the valve arrangement 1 in second position ("activated"). The illustrations of the FIGS. 4b to 4c reproduced on the left, respectively, show the associated enlargements to each illustration on the right.

The valve body 60 has here, exemplary, the shape of a cup or a bowl with bellow-shaped envelope, flat to large extent, comparatively stiff valve tray 60a and with a central and stiff tension rod fastened at the valve tray 60a. By the pre-assembly, the valve body 60 is snapped in by means of the tension rod 62 in a suitable, central snap-in opening of the cap 61.

Notwithstanding the arrangement of the valve body 60 in FIGS. 4a to 4c, the valve body 60 may have the design of a vessel which is open at a front end thereof, wherein a rod tension extends towards the open front end and, when appropriate, protrudes out of it.

The ring front/end 60b of the bellow envelope facing the valve tray 60a is radially positioned in the cap 61 under light prestressing or bias of e.g. about 0.1 mm and axially under preferably larger prestressing or bias of e.g. about 0.5 mm. Thereby the bellow is compressed accordingly and the axial prestressing or bias is maintained above the snapped-in, relatively stiff rod tension 62. The valve is hence centered in a prestressed, complete, free-of-play, radial manner and retains this property also by later activation of the cap 61 and by opening of the valve by means of flowing through of fluids. This axial prestressing or bias may herein be denoted as prestressing or bias of the check valve. This property or feature is only possible when using the cap 61 and it offers or conveys benefits or advantages. Hence, without prestressing or bias, the activation path would have to be selected so large such that it ensures in the present example a sterilization slot of about 0.2 mm in the first position, by taking into account all tolerances and disposable components including the disposable production. Further, the activation path would have to be selected so large such that it comprises, in the first position taking into account all tolerances of all components including the machine, an axial prestressing or bias of the sealing ring of the elastomer component against the (here conical) sealing ring of the valve seat which leads to the desired safe fluid tightness up to the desired opening pressure. By a desired opening pressure of e.g. 180 mbar, an exemplary axial prestress force of about 1 N is required. In the case that the safely realizable activation path of the cap is e.g. 0.8 mm (and the therewith associated gross activation path, retained on machine side, is ca. 1.4 mm) and the tolerances of the pre-assembled or pre-mounted disposable are, summed up together, 0.2 mm, then there will still be 0.4 mm for the actual axial prestressing or bias of the valve in the second position. The middle spring rate of the axial flexibility of the check valve is therefore 2.5 N/mm or 45 mbar/0.1 mm. By an uncertainty of the dimensions of 0.2 mm, this will lead to an uncertainty of the opening pressure of 90 mbar, i.e. of 50% of the set value. By an increase of the fluid flow rate of e.g. 600 ml/min, this would, for example, result in a pressure drop of 600 mbar.

By means of the aforementioned prestressing or bias and a warping or deformation of e.g. 0.4 mm, one advantageously achieves that, by the same path and tolerance relationships as mentioned before, the tension rod 62 in position "activated" of the valve will just safely axially lift up from a ring front end 61a of the cap 61 which is arranged at the tension rod 62. So now the result is: 0.4 mm+0.4 mm=0.8 mm for the actual axial prestressing or bias of the valve. The middle spring rate of the check valve 1 should therefore be now only 1.25 N/mm or 22.5 mbar/0.1 mm in order for the desired opening pressure to again be 180 mbar; this time however with the halved uncertainty of 45 mbar, i.e. of only 25% of the set value. Due to the fact that the spring characteristic line has become flatter, a flatter pressure drop volumetric flow characteristic line is obtained in order to obtain, for example by a flow rate of 600 ml/min, a pressure drop of about 450 mbar. This low pressure drop on the other hand positively acts on the accuracy of the characteristic line and has in addition further positive properties: The pumps in the cassette 900 and in the machine 1000 may, for example by using the herein described check valve, be designed, with corresponding lower pressure, as inlet check valve of the dialysate. The inlet check valve for the venous luer addition may be designed to a smaller opening due to the larger reproducibility of the opening pressure, whereby the operating person requires less efforts for pressing the content of a medication via a syringe into the blood circuit. Due to the fact that this check valve may also be used for the arterial blood return at the completion of treatment, along with the flow velocities, the pressure drops and shear rates decrease as well, whereby the hemolysis is reduced accordingly.

The cap 61, optionally made of the relatively stiff material PP (bending module of elasticity ca. 1750 N/mm), has again the task of absorbing, in a free-of play prestressed manner, the preferably elastomeric valve body 60, which is preferably made of the relatively flexible material of silicon rubber (bending module of elasticity ca. 15 N/mm), to keep it with lower axial tolerance of e.g. +/−0.1 mm in the first position and to transfer it with likewise lower tolerance in the second position, in which a ring surface 61c of the cap 61 facing the film and ring surface 803a of the valve seat 803 touch each other. Thereby, the clearly larger tolerance of the activation path, brought forward from the machine 1000 onto the film 800 via the optional actuator-sensor-matt 950 or directly via actuator 951 (see FIG. 6f), and the associated activation axial force are kept distant and decoupled from the check valve, which is not possible to achieve without the stiff cap 61 positioned between film 800 and valve body 60. Also in the herein represented embodiment of the cap 61, the latter is flushly mounted or fitted or built in, in a simple manner and with its ring front/end surface 61b facing the film, with the film plane of the channel edges of the cassette 900. The cap 61 has radially-extending, radially-protruding and/or radially-rebounded tongues or latches 63. They are accountable for providing the defined and safe frictional-closure retaining of the valve arrangement 1 in the first position (thereby, the present valve design according the present invention may also be, as an optional version, designed such that tongues or pins 63 again radially stick out of the bellows ring front end and thus reaching through into the cap 61 via apertures and ensuring a frictional-closure retaining of the valve position). The spring-tongue or pin functionality shall be described in details with reference to FIGS. 6a to 6d. The cap 61 is, on the other hand, preferably equipped on all sides with numerous drainage and through openings structures, which ensure the safe gas sterilization and ventilation as well as guarantee the pressure-drop-free passage (the amount of pressure drop without a valve is lower than ca. 10 mbar at 600 ml/min).

Figure 5A:
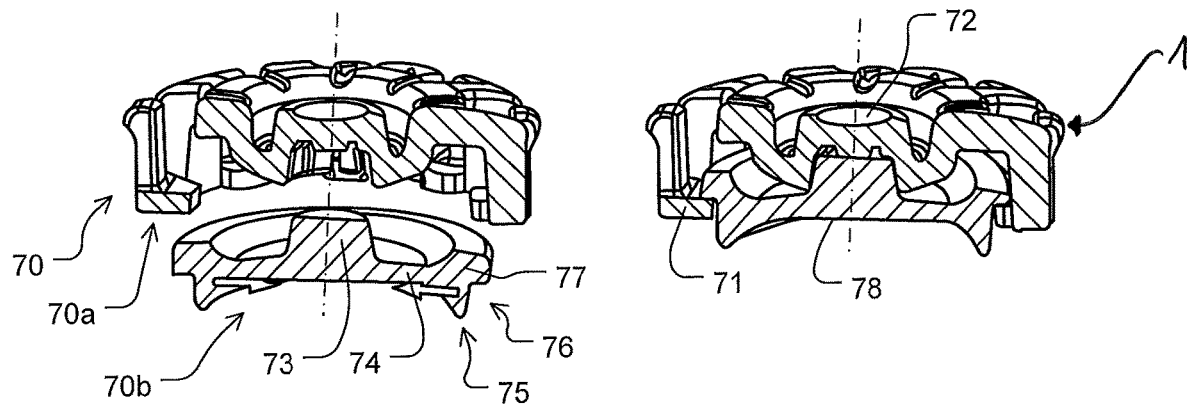
FIGS. 5a to 5d show a further design of a two-piece prestressed check valve with elastomeric valve body and thermoplastic cap in a further embodiment according to the present invention.
Figure 5B:
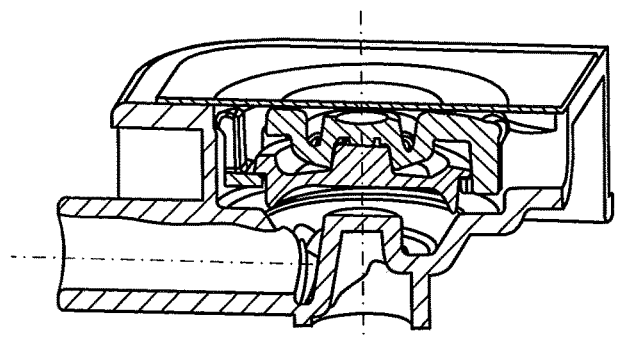
Figure 5C:
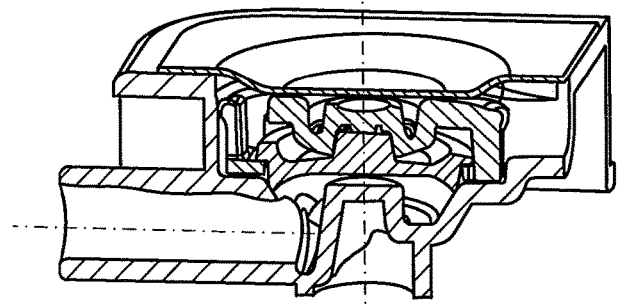
Figure 5D:
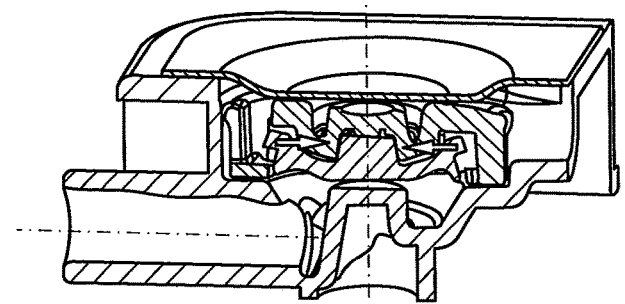

The FIGS. 5a to 5d show a further design of a two-piece, prestressed check valve having an elastomeric valve body and a thermoplastic cap, which are inserted in a valve seat of the functional device according to the present invention. The FIG. 5a shows the valve arrangement in an exploded illustration (left) and assembled (right). The FIG. 5b shows the valve arrangement in prestressed, first position ("initial"), the FIG. 5c shows it in the second position ("activated"), however without flow, and also the FIG. 5d shows it in the second position, however with or during maximum flow.

The cap 70 retains, to a large extent, its design which is known from the aforementioned figures, but comprises now, additionally, retaining protrusions or retaining noses 71 which are protruding, radially to the inside, at the bottom ring front end 70. The exemplary cap 70 of the FIGS. 5a to 5d is designed such that it may be produced by a multiple open-close injection molding tools, with respectively optional, central hot channel injections, and very economically.

The cap 70 comprises a central actuator working surface or contact surface 72, on which an actuator 951 can impact through the film 800.

The valve body 70b comprises a centrally conical mandrel 73, which is free-of-play received in the corresponding cone of the cap 70. A connecting membrane 74 extends between mandrel 73 and a retaining sealing ring 75-76-77.

The valve body 70b comprises, in the non-equipped state or condition, a slight warping of a connection membrane or membrane 78, which is arranged centrally, towards the bottom, (with reference to the illustration in FIG. 5a), or facing away from the film. By the pre-assembly of the valve body 70b in the cap 70 through snapping in the support flange 76 of the retaining sealing ring 75-76-77 until its toothing or interlocking with the retaining noses or lugs 71 of the cap 70, such that the support flange 76 comes to lie on the retaining nose or lug 71, this warping will be already neutralized or the membrane 78 will already be so elastically deformed such that a slight warping in the opposite direction, i.e. to the top, see FIG. 5b, is formed. The warping in the opposite direction is reinforced or intensified by the activation, i.e. by the transfer into the second position, see FIG. 5c, and once again by flow through of treatment fluids, see FIG. 5d.

The retaining seal ring 75-76-77 is, in relation to membrane 78, configured in a compact and/or thick-walled manner. By the axial shifting of the retaining sealing ring 75-76-77, relative to the mandrel 73, a bending stress takes place, on the one hand side, in the membrane 78 which constantly has the effect of warping or deforming the retaining sealing ring 75-76-77 again to the bottom in the originally intended technical injection molding design. On the other hand side, also a hoop tension takes place by the axial shifting of the retaining sealing ring 75-76-77. This hoop tension tries or strives to warp or deform the retaining sealing ring 75-76-77 back to its initial diameter. Thereby the retaining sealing ring 75-76-77 has the largest diameter in the situation by which the membrane 78 is substantially flatly warped and therefore applies compression stress outwardly onto the retaining sealing ring 75-76-77. Once this neutral point is exceeded, the compression pressure decreases again and the retaining-sealing-ring 75-76-77 adds or steers an axial force component which tries to move it or shift it in the opposite position (in direction of the valve opening). This axial force component overlaps with the constantly increasing bending stress in the membrane 78 and leads to a decrease of the spring rate of the valve opening characteristic. Only through the prestress in the cap 70, it is possible to reach sufficiently high paths, by the actual prestress of the valve body 70b in the second position, under which this re-arching effect allows for or enables further flattening of the characteristic line.

The retaining sealing ring 75-76-77 can be a peripheral, radial section which comprises two diameters which are different from each other with a step disposed between them, and which closes, in a section radial thereof, the valve body (i.e. the radial edge)

The FIGS. 5a to 5c show thereby a check valve arrangement 1 in the form of mandrel disc in cap or of an inserted mandrel of the valve body in a cone of the cap which is two-piece, made of elastomer/thermoplastic and seals conically.

The FIGS. 6a to 6d show a further embodiment of the medical functional device according to the present invention, in this case, purely exemplarily, a blood cassette 900 having a check valve arrangement 1. They show in an overall view the parts or elements of the check valve arrangement 1 in a perspectively exploded illustration in half-section. The cassette assembly consists of a half-open treatment cassette 900 or its valve seat 803 which is open to the top, preferably made of PP or other thermoplastic injection molding material, e.g., polyvinyl chloride (in short: PVC) or polycarbonate (in short: PC) and a covering film 800, see FIG. 6a, flushed on the channel edge closing thereby the cassette 900 being however sufficiently flexible, preferably made of PP-TPE laminated or multi-layered extrudates ("TPE" stands for thermoplastic elastomer) or of other flexible extrudate material like e.g. soft PVC or thermoplastic polyurethane (in short: TPU).

The film 800 has a thickness of e.g. 0.24 mm and it is flush at the edge of the peripheral film bar 814 in a welded, glued or compressed manner. The film is preferably flatly arranged in the initial state, i.e. in the first position, so that it can possibly be attached or affixed to the cassette; it can advantageously be dented to the top (i.e. away from the cassette 900) for a particularly little or no stretching stress of the film 800, such that only one dent takes place by the shifting or movement required for the activation. By the flat film arrangement, a stretching of the film of less than 2% is a result of the low activation hub of e.g. 0.8 mm. The cost-effective film type, used here, having little elastomeric proportions can be stretched without the risk of destruction, wherein the film 800 initially takes in a force of ca. maximum 20 N by the valve activation through said stretching. This force is to be at first additionally applied, which reduces to almost zero in the course of treatment through plastic deformation of the film.

Figure 6A:
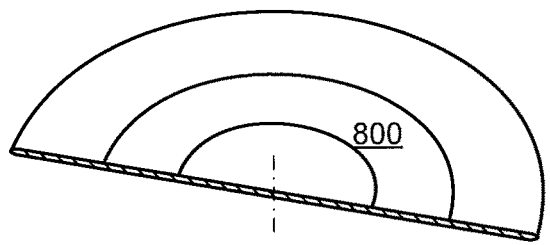
FIGS. 6a to 6d show a further embodiment of the medical functional device according to the present invention, here purely exemplary a cassette, having a check valve arrangement in an exploded view.
Figure 6B:
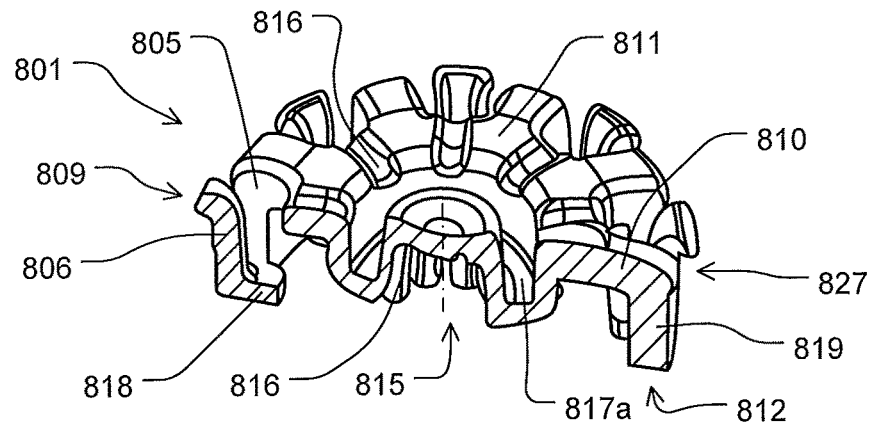
Figure 6C:
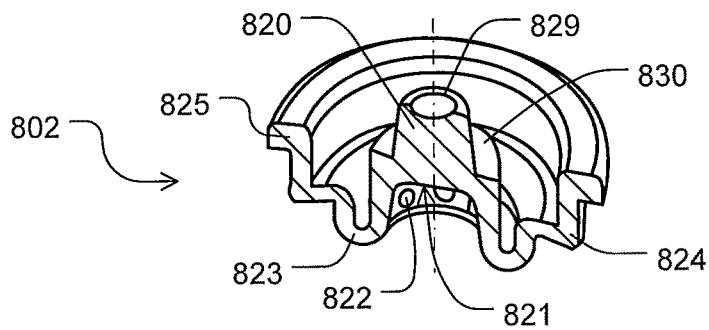
Figure 6D:
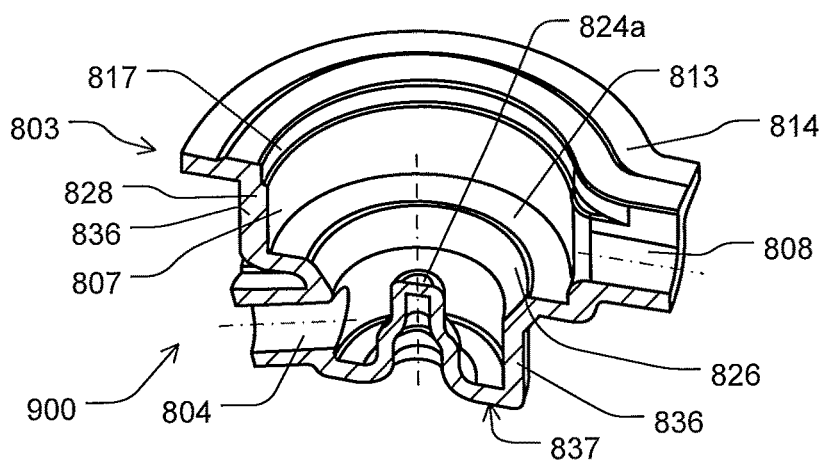

The valve seat 803 of FIG. 6d is exemplary geometrically configured or designed so that it does not comprise any undercuts as an injection molding for the demolding process. Due to the fact that the function of the check valve in the treatment cassette 900 relates always to fluids which arrive from hose lines and should flow into the cassette 900, cassette 900 anyhow needs a cylindrical pipe arrangement 804 at the relevant points or places. The cylindrical pipe arrangement 804 open via a hole into the channel and chamber arrangement of the cassette 900 (i.e. herein into the lower area of the valve seat 803). Insofar, almost no additional costs shall arise for integrating the check valve-valve seat of the illustrated design in cassette 900

The valve seat 803 contains at least one outgoing fluid channel 808.

The valve seat 803 in fixing or activation direction is particularly designed in a stiff way through cylindrical, almost vertical cylinder walls 836 and through a wide valve seat support front/end 837, which can be a peripheral surface and which can be disposed vertically or substantially vertically at or on the cylinder walls 836 and/or can merge into those.

The—only preferably cylindrical—pipe arrangement 804 can open into the cylindrical walls 836.

The outgoing fluid channel 808 preferably gets loose above the cylindrical walls 836.

The valve arrangement 1 consists of the cap 801 (preferably made of PP or made of other relatively stiff thermoplastic injection molding material like PC or hard PVC), see FIG. 6b, and the valve body 802, see FIG. 6c (preferably made of LSR (Liquid Silicon Rubber), a cost-effective mass of elastomer having sufficient low compression set, good resistance to sterilization and good hemo-compatibility.

The cap 801 has the shape of an arch having several openings or through-openings 805 which are radially to the outside and axially to the top open. In those openings or through-openings, snap-in tongues or pins 806 are arranged. They can be radially bent to the inside, for example, with low force of ca. 1 N per 0.2 mm radial deflection. The snap-in tongues or pins 806 close the openings or through-openings only partially, e.g., to ca. 30%.

In the preferred embodiment, the number of the openings or through-openings 805 and the number of snap-in tongues or pins 806 is preferably uneven, respectively, because uneven division increase the exactness of centering of the cap 801 in the valve seat 803 (two two-dimensionally centering openings or through-openings 805 always face a snap-in tongue or pin 806 in those exemplary embodiments or the latter is neighbored by each of them while retaining a split or slot. The number of openings or through-openings or snap-in tongues or pins 806 is preferably 9 and can be advantageously within the range of 7 to 11 by a valve seat outer diameter of 33 mm.

Due to the relatively large number of openings or through-openings 805 or snap-in tongues or pins, it is possible to mount the valve arrangement 1 in the valve seat 803 without specified or determined orientation of rotation. Even when preferably vertical or substantially vertical cylindrical walls, herein denoted as cap reception valve seat cylindrical walls 807 and 817, are interrupted at one to three points through outgoing fluid channels, the remaining wall segments of these cylindrical walls or of the valve seat 803 are sufficient enough to sufficiently center or align the cap 801, to maintain it in the desired positions and to achieve throughout the openings or through-openings 805 a sufficiently low flow resistance for the treatment fluid.

With maximum flow of about 600 ml/min, the mere flow resistances of the cap 801 in the mounted and activated state are, e.g., at ca. 20 mbar and comprise therefore only ca. 4 to 5% of the total flow resistance with mounted flowed-in check valve 1.

The cap 801 is preferably designed such that it can be cost-effectively produced in an open-close injection molding without a slide valve and with high number of cavities. It constitutes so far the most cost-effective, found or realized design of the remanent activatable check valve of a functional device 900 according to the present invention.

The cap 801 comprises a peripheral, preferably sharp edge, denoted with reference numerals 809 and 827, which is on the same level of the preferably with a U-shaped support arch 810 being open to the bottom which grants or reinforces stability to the cap 801, and the bendable or flexible snap-in tongues or pins 806 and thus building the separation plane of the injection molding. Due to the fact that by injection molding elements or components (above all when they are produced by means of multi-cavity molding) edges and mismatch in mold always occur in the main separation plane, a virtue is made out of necessity herein, in that the sharp angle of the edge and the systematical and radial mismatch in mold, included in the construction in the form of the edge or angle, as a functional element, planned or intended to be the valve function (elaboration further below).

An upper surface or plane, denoted herein also as upper cap front end 811, forms the highest section or part of the vaulted or arched construction, which includes support arches 810, and represent through the film 800 the mechanical interface for the introduction or initiation of activation force, activation path and support force by the actuator-sensor-unit (abbreviated: ASE) of the machine 1000. The upper surface or plane represents through preferably radial structuring grooves 816 uninterrupted, preferably flat ring front ends, whose diameter can be in the range of 6.5 to 8.5 mm. Thereby, the diameter and the size or dimension of the ring front end, being the effecting contact surface for an actuator 951 (see FIG. 6*f*) during the activation, are within a range which is advantageous for providing the activation hump (not illustrated) of the actuator-sensor-unit with enough transition area for force and path, however to be at the same time distant enough from the maximum seat diameter of 13 mm. In this way, on the one hand side, the stretching of the film 800 by the activation (transition into the second position) is limited and, on the other hand side, the activation force which is to be transferred and, solely expended for the stretching of the film 800 is minimized and thereby a ring-shaped fluid space remains between the film 800 and the arch of the cap 801, after activation, which connects the through-openings 805 within each other by sufficient low flow resistance and with the inwardly or outwardly extending channels.

A surface or plane closing or covering the cap 801 to the bottom, herein also referred to also as lower cap ring front end 812, builds up together with a preferably peripheral or closed support surface of the valve seat 803, for the lower snap-in ring front end 812, a functional system for ensuring a short activation path and precise constant condition of the cap 801, when the valve is in the second position.

Both on the upper ring front end 811 and in the area of the cone reception or intake 815 (which receives a centering cone 820 of the valve body in the operating state), the cap 801 comprises, optionally, several structurings such as structuring grooves 816, notches and rebounds which are needed for the sterilization gases to sufficiently reach many surface parts of the cap 801, the valve body 802 and the cylinder walls 807 and 817 of the valve seat 803.

In order for the element or component to sustain a symmetrical and an unremarkable warpage, these outer and inner structurings are arranged in a concentrical and even or equal number, divided in relation with the number of the through openings 805/snap-in tongues or pins 806. Due to the fact that number of the latter is preferably an uneven number, one can see in each half-section illustration or drawing (or in each front section through the middle point of the cap 801), on the one side (right or left), a snap-in tongue or pin, an arch or a support tongue or pin or a section thereof, while this is not the case on the opposite side due to asymmetry. This illustration in section should however not lead to the misunderstanding/misinterpretation that at a certain point or place, structures or supports are missing or elements or components hang unsupported in midair. Rather, there is an even distribution of material contact and non-contact through surface and extent.

Not only the arch or vaulted structures 810 contribute to the stiffness of the cap 801, rather also preferably, radial to the outside, provided vertical cylinder walls 819 and the preferably peripheral walls, which are steeply conical, inside and outside of the peripheral slot, herein referred to as cap centering groove 817*a*. One obtains a structure with relatively even wall thickness by high axial stiffness. An axial force of 60 N on the upper ring front end 811 of the cap 801, by support on the lower ring front end 812 of the cap 801, leads merely to a lowering of the preferably central cone reception 815 of about 0.04 mm.

The diameter of the cylinder wall 807 of the valve seat 803, at which the edge 809 of the cap 801 abuts, in the second position, not in the first position, is definably designed as larger than the stiff outer diameter of the cap 801, at the edge 827 of the arch 810, and as larger than the stiff outer diameter of the cap 801 at the chamfered peripheral edge towards the lower ring front end 812. With such play-design, the cap 801 may be tilted to up to 6 degrees, without canting at both hard diameters against the hard cylinder wall 807. A tilting of the cap of more than 3.4 degrees, are mechanically, through a tilted activation, not realizable anyhow.

The valve seat 803 comprises a snap-in level or step 828, which is disposed in the path from the cylinder wall 836 to the snap-in reception valve seat cylinder wall 817. It represents a diameter tapering or diminution to the interior of the valve seat 803.

The valve body 802 has, optionally, a rolling-bellows form and encompasses, again optionally, the functional elements: A centering cone 820, which is preferably centrally arranged and ascends towards the cap 801 up to a front end surface 829 or locks up thererwith, a support front end 821, against which, in the second position, a centering stop mandrel or fold 824*a* of the valve seat 803 strikes or bends, at least one auxiliary centering hump 822, which, at least in the second position, touches the centering stop mandrel or fold 824*a*, and a spring membrane 823, which is provided in a form of a peripherally closed (i.e. exemplary circular) however open to the top (with regard to the illustration of the figures in the mounted state). The valve body comprises further a preferably peripheral support or retaining ring 825 protruding radially outwards, which can only protrude through the tips of the centering mandrel, and which is the section of the valve body 803 protruding furthest to the radial.

In a preferred embodiment the build-in opening of the valve seat 803 has a largest diameter of 13 mm (at the point of the film layer).

The centering 820 is, as seen in FIG. 6*c*, in certain exemplary embodiments according to the present invention, a centrally arranged truncated cone. Its cone envelope surface serves preferably both as introduction chamfer into the associated centering cone area or the cone reception 815, by the assembly, as well as radial centering towards cap 801 with defined low residual clearance.

The stop front end is in specific exemplary embodiments according to the present invention centrally arranged and can form the bottom surface of the truncated cone of the centering cone 820. In connection with the centering stop mandrel or fold 824a of the valve seat 803, both an axial, low play-restricted restriction of the check valve as well as a movement stop by extreme operating pressures in the reverse direction of the check valve take place.

The optional, auxiliary centering humps 822 form, in certain exemplary embodiments according to the present invention, together with the often rounded, substantially cylindrical envelope surface of the centering stop mandrel or fold 824a, in an advantageous manner, a further, usually slightly play-restricted, radial centering arrangement. The latter may, e.g. by means of the assembly procedure, contribute (or be responsible for) so that a tilting of the check valve in the valve seat 803 is prevented, at the same time however, that during the operation a possibly low effect or influence on the opening characteristic is exerted.

The springy connection membrane or spring membrane 823 may advantageously be similar to rolling bellows. It can be advantageous for the correct positioning or fitting of the sealing ring 824 in both operation states or positions: Due to the fact that it is bendable or flexible, axial prestressings or bias and axial operation prestressings or bias of the sealing ring 824 may build up against the sealing ring zone 826. Thereby, the spring membrane 823 may radially form a fluid-tight zone up to the sealing ring 824. Ultimately, the spring membrane 823 can hold also the support or retaining ring 825, under prestressing or bias, onto the retaining lug or support tongues or pins 818, and it can align the support or retaining ring 825 radially, during the mounting and during the operation position in an open flow direction.

As seen in the FIGS. 6a to 6d, the cap 801 brings the valve body 802, already by the factory-made insertion of the valve body 802 in the cap 801, in an elastically prestressed position, namely as soon as the valve body 802 is engaged in the snap-in 801.

The prestressed force, achieved in this way, is preferably just under the pressure or the force dimensioned, by which the valve should open when used as intended.

The person having skill in the art, realizes already from FIG. 6c what FIGS. 6e to 6h show in details, namely that the spring membrane 823 may act or effect as spring or resetting element, when the valve body 802 in FIG. 6c is engaged in the cap 801 in FIG. 6b. In case the valve body 802 is engaged in the cap 801, the valve body 802, prestressed by means of the spring membrane 823, retains or supports itself, on one hand side, with support ring 825 behind the support tongues or pins 818 and on the other hand side with the centering cone 820 in the cone reception 815. In this condition, the spring membrane 823 is elastically prestressed, because the valve body 802 is forced, due to the dimensioning of valve body 802 and cap 801 in the equipped state, into the elastically prestressed condition through form closure.

When the cap 801, together with the valve body 802 being engaged in it, is inserted in the valve seat 803 in FIG. 6d such that the snap-in tongues or pins 806 are disposed in the valve seat wall or in the cap reception valve seat cylinder wall 817, in this case, a slot, of width b, is found between the sealing surface or sealing ring zone 826 of the valve seat 803 and the sealing ring 824 of the valve body 802. Between the support tongues or pins 818 and the valve seat stop ring support 813 a further slot, of width a, is thus present. When both slots are present (i.e. both are open or detectable), then the first position, which is suitable for the gas sterilization according to the exemplary embodiment of the present invention, is present or achieved. The slot b may be smaller or narrower than the slot a.

Through an impression of path/a shifting and/or movement or a force larger than the prestressing force on the cap 801, which is effected by pressing an actuator 951 onto the film 800, the slot b can be closed when or in that the sealing ring 824 is tightening-pressed or sealing-pressed onto the sealing surface 826. Thereby, it is assumed or expected that the cassette 900 is mounted stationary and the cap 801, having the valve body 802, is movable/adjustable relative to the valve seat 803. If the slot b is closed, then the second position of the exemplary present embodiment is available is present or achieved.

The cap 801, having the valve body 802 inserted in, is, due to the through openings 805 of the cap 801, permeable to fluid such that the fluid coming from the side and/or from the top may penetrate through the cap.

The required impression of path/shifting or movement for opening and closing the valve is very small, e.g. only 0.8 mm, between closed and open position in the embodiment example according to FIGS. 6a to 6d. That allows a very flat spring characteristic line of the spring membrane 823 in connection with the prestressing or bias. The desired sealing force with which the sealing ring 824 should be tightening-pressed onto the sealing surface 826, is thus already achieved with very small impression of path and slightly changes with an increasing impression of path. As soon as the sealing ring 824 pushes against the sealing surface 826 due to an impression of path, a sealing force, according to a jump function or a step function or a discontinuous function, is available abruptly or in a step-wise manner.

Figure 6E:
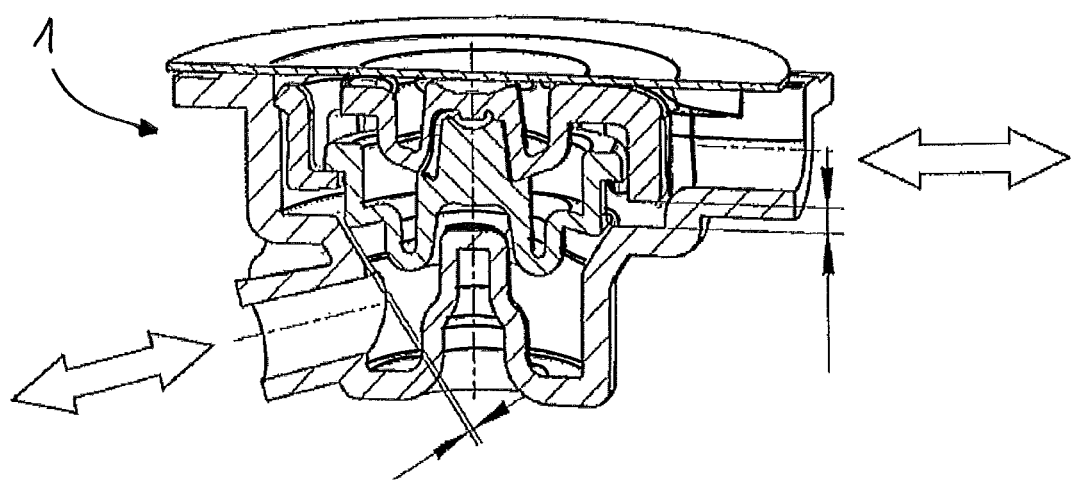
FIGS. 6e to 6h show the embodiment of FIG. 6a to FIG. 6d in a jointed state in different valve positions.
Figure 6F:
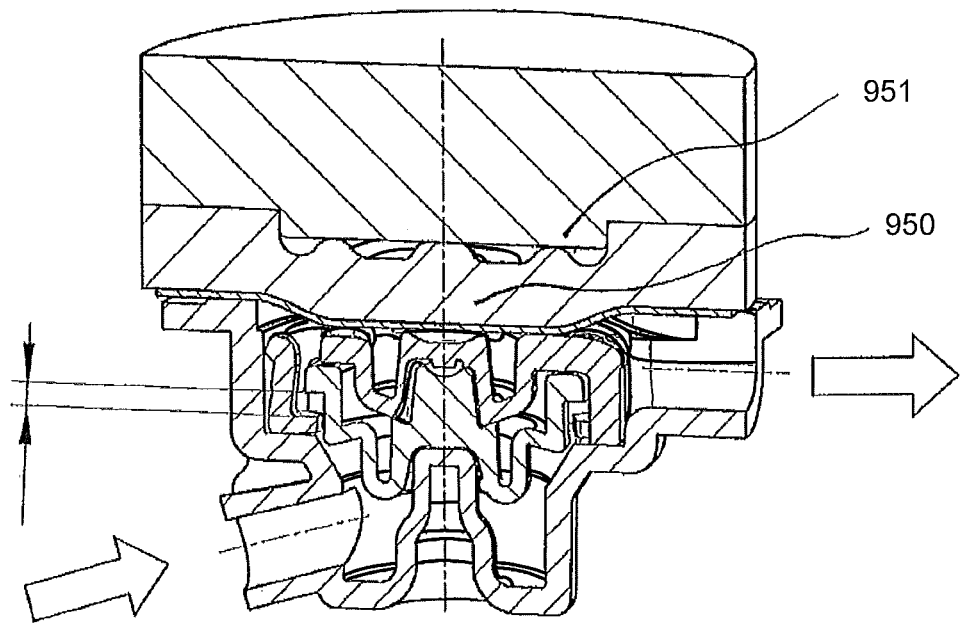
Figure 6G:
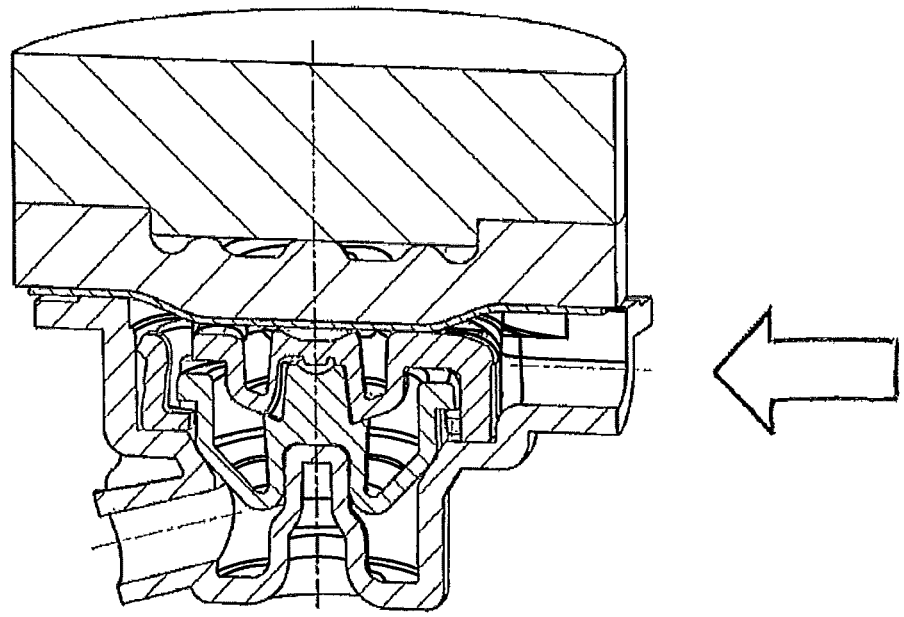
Figure 6H:
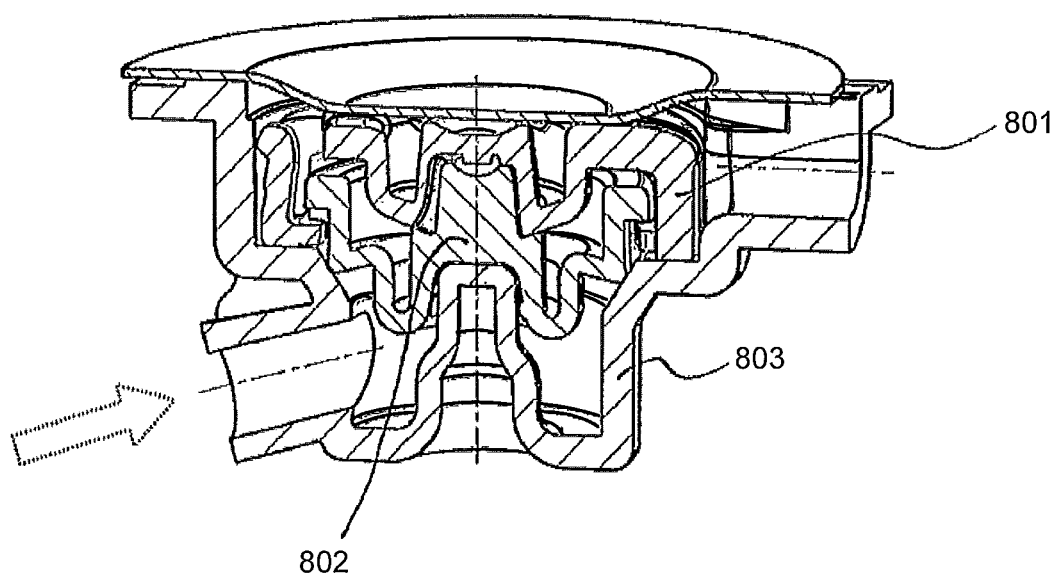

The FIGS. 6e to 6h show the embodiment of FIGS. 6a to 6d in a merged or assembled state in different valve positions. FIG. 6e show them in the first, initial position prior to the closing of a machine door, FIG. 6f show them in the second, activated position by closed machine door by maximum volumetric flow of the treatment fluid, FIG. 6g shows them in the second, activated position by maximum sealing pressure of the treatment fluid and FIG. 6h shows them in the activated, second position by open machine door, following the removal of the cassette 900 from the treatment device.

In the FIGS. 6e to 6h, the big arrows indicate the volumetric flows; the small ones indicate slots which may be formed between the concerned elements or components.

The prestressing or bias of the valve body 802 results, in the example of FIGS. 6a to 6h, from the fact that the valve body 802 is supported by means of its support or retention ring 825 onto the support tongues of pins 818 of the cap 801. Furthermore, its centering cone 820 sits closely at the cone reception 815. In the position shown in FIG. 6h, the valve body 802 is however not supported onto the support tongues or pins 802 anymore. A tension of the valve body 802 arises by the involvement of the sealing ring 824 of the valve body 802, which supports itself onto the sealing ring zone 826 of the valve seat 803.

LIST OF REFERENCE NUMERALS 1 check valve arrangement
21 diameter landing or change
30 valve body
31 core cylinder
32 radial sealing bar 32a closed or peripheral sealing edge
32b cup envelope
32c closed or peripheral split or slot
32d split or slot base
33 guiding clamping drainage ribs
34 clamping guiding knobs
35 clamping snap-in knobs
36 drainage bottom ribs
37 sealing cylinder
38 guiding cylinder
39 snap-in layer
40 valve body
41 positioning ring
41a drainage structures
41b upper ring front surface
41c lower ring front surface
42 inlet ring zone
43 sealing ring zone
44 core area
45 conical sealing seat
46 plunger
50 valve body
50a drainage structures
51 cap
51a drainage structures
51b activation front/end surface
52 sealing ring
53 knobs
54 openings or through-opening
55 ribs of the valve base
57 retaining head
58 ring front/end surface
59 ring front/end surface
60 valve body
60a valve tray
60b ring front/end surface of the valve body
61 cap
61a ring surface
61b ring front/end surface facing film
61c ring surface facing film
62 tension rod
63 pins
70 cap, exemplarily embodied as a snap-in cap
70a lower ring front/end
70b valve body
71 notches
72 hot channel injections
73 conical mandrel
74 connecting membrane
75-76-77 support sealing ring
76 support flange of the support sealing ring
78 membrane
800 film
801 cap
802 valve body
803 valve seat
803a ring surface
804 pipe assembly
805 openings or through openings
806 snap-in pin
807 cap reception valve seat cylinder wall
808 fluid channel
809 sharp edge
810 static supporting arch or vaulted structures
811 upper cap ring front
812 lower cap ring front
813 valve seat limit stop ring support
814 film bar
815 core reception
816 structuring grooves
817 cap reception valve seat cylinder
817a cap centering groove
818 support pin
819 vertical cylinder walls
820 centering cones
821 stop front end
822 auxiliary centering humps
823 spring element, embodied as spring membrane
824 sealing ring
824a—centering stop mandrel or fold
825 retaining ring
826 sealing ring zone
827 sharp edge
828 snap-in layer of the valve seat
829 front end surface
830 hard body
831 connector-sided space
836 cylinder wall
837 valve seat support front/end
900 cassette or medical functional device
950 actuator-sensor-mat
951 actuator
1000 dialysis machine, machine, blood treatment apparatus

The invention claimed is:

1. A medical functional device comprising:
    a valve comprising:
        a valve seat comprising a sealing cylinder; and
        a valve body comprising a cap, a valve core cylinder and drainage ribs extending along and attached to the valve core cylinder, wherein the valve body is configured to:
            transfer from a first position into a second position when a force external to the medical function device is applied onto the valve body such that the valve body is moved or shifted relative to, and within the sealing cylinder of the valve seat; and
            latches, in a self-retaining manner due to friction between: the drainage ribs of the valve body and the sealing cylinder of the valve seat, in the second position after release of the force following a transfer into the second position
    wherein the first position is suitable for gas sterilization of the medical functional device because, while the valve body is in the first position, fluid can flow through the valve in a first direction and in a second direction that is opposite of the first direction, and
    wherein the second position is a functional position that provides a check valve function because, while the valve body is in the second position, fluid can flow through the valve in the first direction only; and
    wherein the drainage ribs are configured for guiding and clamping the valve body within the valve seat and for draining the fluid from the valve core cylinder.

2. The functional device according to claim 1 wherein the valve is configured to be transferred from the first position into the second position when the force is applied onto the valve body by an actuator of a blood treatment apparatus, and wherein the functional device is configured to be connected to the blood treatment apparatus.

3. The functional device according to claim 1, wherein the valve body further comprises a plurality of knobs extending radially from openings or through-openings of the cap when the cap is connected to the valve body.

4. The functional device according to claim 1, further comprising a snap-in position or step or a step-like or stacked diameter restriction within the sealing cylinder of the valve seat.

5. The functional device according to claim 4, wherein the snap-in position, the step or step-like or stacked diameter restriction is in an area in which a closed or peripheral section of the valve body lies in the valve seat.

6. The functional device according to claim 1, wherein the valve body, or the cap, seal in the second position against the valve seat in a sealing area, and wherein the valve seat is configured, in the sealing area, in a conical, cylindrical or flat manner.

7. The functional device according claim 1, wherein the valve body is positioned in the cap, radially under a first prestressing or bias and axially under a second prestressing or bias, and wherein the second prestressing is larger than the first prestressing.

8. The functional device according to claim 1, wherein the valve body has the shape of a container or a cup and further comprises a valve tray comprising a tension rod, which is optionally centrally and stiffly fastened to the valve tray, and wherein the tension rod is configured to connect the valve body with the cap by engaging a snap-in opening of the cap.

9. The functional device according to claim 1, wherein the cap further comprises radially extending tongues or pins or axially extending and radially deformable tongues or pins.

10. The functional device according to claim 8, wherein the tension rod and the valve tray are sufficiently stiff so that, in the second position, the tension rod maintains contact-free space to other sections in all spatial directions in the cap.

11. The functional device according to claim 1, wherein the cap has an arched shape having several openings or through-openings which are open radially and axially at a top of the cap, and wherein snap-in tongues or pins are arranged in the openings or through-openings and are configured to only partially close the openings or through-openings when radially inwardly bent.

12. The functional device according to claim 11, wherein the cap further comprises a closed or peripheral edge located at the level of the snap-in tongues or pins, configured for providing a main separation plane for injection molding.

13. The functional device according to claim 1, further comprising a closed or peripheral sterilization split or slot that remains in the first position, and which is closed in the second position, and wherein the first position, which is an axial mounting position, and the sterilization split or slot is maintained through friction closure between components at clamping-aligning ribs.

14. The functional device according to claim 1, wherein the device is configured for use as a blood cassette, blood tube or infusion tube.

15. The functional device according to claim 1, wherein the device further comprises a blood cassette comprising a hard body and a film covering the hard body or parts thereof, wherein the valve seat is provided in the hard body, and wherein the valve body can transfer into the second position by at least one of pressure on the film or by moving or shifting an actuator of a blood treatment apparatus towards the film.

16. The functional device according to claim 15, wherein the film-sided front end surface of the valve does not project beyond the film plane of the blood cassette.

17. The functional device according to claim 1, wherein the valve or a section thereof is configured to effect a prestressing or bias of the valve body inserted into the valve seat or of at least a section thereof.

18. The functional device according to claim 17, wherein the prestressing or bias is effected by a spring element.

19. The functional device according to claim 18, wherein the spring element is a section of the valve body.

20. A medical functional device comprising:
a valve comprising:
a valve seat comprising a sealing cylinder; and
a valve body comprising a valve core cylinder and drainage ribs extending along and attached to the valve core cylinder, wherein the valve body is configured to:
transfer from a first position into a second position when a force external to the medical function device is applied onto the valve body such that the valve body is moved or shifted relative to, and within, the sealing cylinder of the valve seat; and
latch, in a self-retaining manner due to friction between the drainage ribs of the valve body and the sealing cylinder of the valve seat, in the second position after release of the force following a transfer into the second position
wherein the first position is suitable for gas sterilization of the medical functional device because, while the valve body is in the first position, fluid can flow through the valve in a first direction and in a second direction that is opposite of the first direction, and
wherein the second position is a functional position that provides a check valve function because, while the valve body is in the second position, fluid can flow through the valve in the first direction only; and
wherein the drainage ribs are configured for guiding and clamping the valve body within the valve seat and for draining the fluid from the valve core cylinder.

21. The device of claim 20, further comprising a snap-in position or step or a step-like or stacked diameter restriction within the sealing cylinder of the valve seat, and wherein the snap-in position, the step or step-like or stacked diameter restriction is in an area in which a closed or peripheral section of the valve body lies in the valve seat.

22. The device of claim 20, the valve defining a sterilization split or slot while the valve body is in the first position.

23. The device of claim 20, wherein the device further comprises a blood cassette comprising a hard body and a film covering the hard body or parts thereof, wherein the valve seat is provided in the hard body, and wherein the valve body can transfer into the second position by at least one of pressure on the film or by moving or shifting an actuator of a blood treatment apparatus towards the film.

24. The device of claim 20, wherein the valve or a section thereof is configured to effect a prestressing or bias of the valve body inserted into the valve seat or of at least a section thereof.

* * * * *